United States Patent
Siddiqui et al.

(10) Patent No.: US 6,403,110 B1
(45) Date of Patent: Jun. 11, 2002

(54) TOPICAL TREATMENT FOR OILY SKIN

(75) Inventors: Mukhtar Siddiqui, San Ramon; Rita W. Ayer, Santa Clara; Yoshi Kawasaki, San Francisco, all of CA (US)

(73) Assignee: Shaklee Corporation, Pleasanton, CA (US)

( * ) Notice: Subject to any disclaimer, the term of this patent is extended or adjusted under 35 U.S.C. 154(b) by 0 days.

(21) Appl. No.: 09/635,293

(22) Filed: Aug. 9, 2000

(51) Int. Cl.[7] .............................. A61K 7/00; A61K 7/48; A61K 7/02
(52) U.S. Cl. ................. 424/401; 424/78.02; 424/78.03; 424/45
(58) Field of Search .............................. 424/401, 78.02, 424/45

(56) References Cited

U.S. PATENT DOCUMENTS

| | | | | |
|---|---|---|---|---|
| 3,024,244 A | * | 3/1962 | Pollak | 260/295 |
| 5,472,699 A | * | 12/1995 | Duffy et al. | 424/401 |
| 5,478,560 A | * | 12/1995 | Tominaga et al. | 424/401 |
| 6,106,818 A | * | 8/2000 | Dulog et al. | 424/401 |
| 6,143,310 A | * | 11/2000 | Sang et al. | 424/401 |
| 6,150,403 A | * | 11/2000 | Biedermann et al. | 424/7 |

OTHER PUBLICATIONS

Barnet Products Corp., "Zincidone" Product Disclosure, 560 Sylvan Avenue, Englewood Cliffs, NJ 07632.
Kniewald et al., *Endocr. Regul.* 1992 Mar.; 26 (1):47–51.
Tully et al., *FASEB J.* 1994 Mar. 1; 8 (3):343–9.

\* cited by examiner

*Primary Examiner*—Diana Dudash
*Assistant Examiner*—Mina Haghighatian
(74) *Attorney, Agent, or Firm*—Klarquist Sparkman, LLP

(57) ABSTRACT

A method of reducing sebum on the surface of skin is provided. The method includes applying topically to the skin a composition comprising an alcohol, pyridoxine hydrochloride or a salt or derivative thereof, and a zinc salt, wherein the composition is applied to the surface of the skin in an amount sufficient to reduce sebum. A topical composition for reducing sebum on the surface of the skin, comprising an alcohol, pyridoxine hydrochloride or a salt or derivative thereof, and a zinc salt in an amount sufficient to reduce the amount of sebum on the surface of the skin is also described.

1 Claim, 8 Drawing Sheets

TOPICAL TREATMENT FOR OILY SKIN

FIELD OF THE INVENTION

This application relates to the field of compositions for the treatment of oily skin, more specifically to a topical treatment for the skin to reduce sebum.

BACKGROUND OF THE INVENTION

There are three major facial skin types: (1) skin that is slightly to extremely oily; (2) skin that is slightly to extremely dry; and (3) skin that is slightly to extremely oily across the forehead and down the nose to the chin (the so-called T-zone) and simultaneously slightly to extremely dry across the rest of the face.

In order to treat dry skin to reduce the tightness, flakiness and scaliness, humectants and emollients are used.

However, there are no such ready treatments for oily skin. Skin oils, which are properly called sebum, can be removed by applying low molecular weight alcohols, such as ethyl alcohol or isopropyl alcohol. Alternatively, the skin can be cleansed with soaps or surfactants. Usually, these techniques offer only a temporary reprieve from the oiliness, since the removed sebum is readily replaced by an abundant reservoir of oil residing in the sebaceous glands just below the surface of the skin.

Sebum is a secretion of the sebaceous gland. This gland is found in the epidermis of the entire body except for the palms of the hands, the soles and dorsal (upper) surfaces of the feet. They are found in their highest numbers on the head, particularly on the face and the scalp (Strauss, J. S. and Pochi, P. E. In: Gans, O., Steigleder, G. K., eds. Hanbuch der Haut-und Geschlechtskrankheiten; Normale und Pathologische Anatomie der Haut I. Berlin: Springer-Verlag, 1968:184–223; Wilkinson, J. B. and Moore, R. J., eds. Harry's Cosmeticology, 7th ed. New York:Chemical Publishing, 1982). The amount of sebum produced by these glands is controlled by endogenous hormones, especially particularly the sexually related hormones such as testosterone, and therefore varies from one individual to another. Sebum flow is also controlled by a variety of other factors, such as temperature and humidity (Stauss, J. S., Downing, D. T., and Ebling, F. J. In: Goldsmith, L. A., ed. Biochemistry and Physiology of the Skin. New York: Oxford University Press, 1983:569–595).

Hormonal control is at least partially under the influence of an enzyme, namely 5-alpha reductase, that converts testosterone to dihydrotestosterone, which effects the production of sebum. Levels of sebum produced by the sebaceous glands are normally highest during the teenage years. In women, the output of sebum normally decreases after menopause. The level remains relatively unchanged into old age in men (Pochi, P. E., Strauss, J. S., and Downing, D. T., J. Invest. Dermatol. 73:108–111(1979)).

Sebum is composed of triglycerides, diglycerides, free fatty acids, wax esters, squalene, cholesterol and cholesterol esters (Greene, R. S., Downing, D. T., Pochi, P. E., and Strauss, J. S., J. Invest. Dermatol. 54:240–247(1970)). Although the function of sebum is believed to be primarily in helping to maintain the skin's barrier integrity, it also is known to have mild bactericidal and antifungal properties (Kligman, A. M. In: Montagna, W., Ellis, R. A., and Silver, A. F., eds. Advances in Biology of Skin:The Sebaceous Glands, Oxford, England: Pergamon Press, 1963: 110–124). Sebum is also well know to protect the hair shaft from damage brought about by brushing, combing and styling of the hair (Agache, P. G. In:Zviak, C., ed. The Science of Hair Care. New York: Marcel Dekker, 1986: 469–500).

There are two primary ways that sebum is believed to affect the severity of acne. The first is that excess sebum can contribute to the packing of horny skin cells at the opening of the sebaceous follicle on the surface of the skin. This abundance of dead skin cells causes a constriction in the follicular opening ultimately leading to a plug or comedone.

A comedone is one of the earliest physical manifestations of acne. Furthermore, once the comedone is formed, regardless of its origin, it is normally found to be populated with an anaerobic microorganism, namely *Propionibacterium acnes* (*P. acnes*). The sebum in the follicle provides an excellent growth medium for this organism. The products of the growth of *P. acnes* on sebum results in the generation of free fatty acids that are irritating to the skin and have been shown to be acneogenic. If a break in the thin walls of follicle occurs, these microbially-derived irritants can escape into the surrounding epidermal and surrounding dermal tissue producing significant irritation and therefore redness and tissue damage. This latter effect of sebum on acne is believed to be one of the principal sources of the redness of acne.

Therefore, for both cosmetic and dermatological reasons, the ability to reduce the presence of sebum on the skin is important. An even greater effect would be to reduce the amount of sebum on the surface of the skin initially as well as to reduce it for a significant period of time following a topical treatment.

Thus, a significant amount of research has been devoted to identifying ways to reduce sebum on the skin. Many different approaches have been tried, most with only limited success. The primary approach has been to try to avoid putting oils on the surface of the skin. Such "oil-free" approaches have met with little success. However, by providing products to apply to their skin that do not feel oily or greasy, consumers believe that they are taking positive steps to avoid making the skin more oily than normal.

Numerous products have been developed that contain materials to absorb the oils secreted by the sebaceous glands. These products contain materials such as starches, clays, silica, and even porous polymer beads that bind surface skin oils. Although these products actually exhibit some efficacy in absorbing sebum, they are difficult to deliver to the skin in sufficient quantities to absorb a significant quantity of sebum without radically detracting from the form or feel of the formulation. Therefore, this method of sebum reduction often results in products that are either less effective than needed or less aesthetically appealing to consumers. Therefore, there is a definite need for better, more technically advanced methods to reduce sebum on the skin.

SUMMARY OF THE DISCLOSURE

Currently techniques for treating oily skin offer only a temporary reprieve from the oiliness, since the removed sebum is readily replaced by an abundant reservoir of oil from the skin. For both cosmetic dermatological reasons, the ability to reduce the presence of sebum on the skin is important. Described herein are novel compositions and methods which reduce the amount of sebum on the surface of the skin after initial application, and continue to reduce the presence of sebum on the surface of the skin for a significant period of time following a topical treatment.

A method of reducing sebum on the surface of skin is provided. The method includes applying topically to the skin a composition that includes an alcohol, pyridoxine hydrochloride or a salt or derivative thereof, and a zinc salt, wherein the composition is applied to the surface of the skin in an amount sufficient to reduce sebum.

In one embodiment, the method includes applying a composition that includes alcohol as about 0.01 to 40% by weight of the composition, pyridoxine hydrochloride, or a salt or derivative thereof, as about 0.00001% to 5% by weight of the composition, and zinc salt as about 0.0001 to 10% by weight of the composition. In one specific, non-limiting example, the alcohol is present as about 10% by weight of the composition, the zinc salt is present as about 0.5% by weight of the composition, and the pyridoxine hydrochloride is present as about 0.05% by weight of the composition.

Other embodiments also include a topical composition for reducing sebum on the surface of the skin, wherein the composition includes an alcohol, pyridoxine hydrochloride or a salt or derivative thereof, and a zinc salt in an amount sufficient to reduce the amount of sebum on the surface of the skin.

In another embodiment, the composition includes alcohol as about 0.01 to 40% by weight of the composition, pyridoxine hydrochloride, or a salt or derivative thereof, as about 0.00001% to 5% by weight of the composition, and zinc salt as about 0.0001 to 10% by weight of the composition. In one specific, non-limiting example, the alcohol is present as about 10% by weight of the composition, the zinc salt is present as about 0.5% by weight of the composition, and the pyridoxine hydrochloride is present as about 0.05% by weight of the composition.

DETAILED DESCRIPTION OF SPECIFIC EMBODIMENTS

Figure 1:
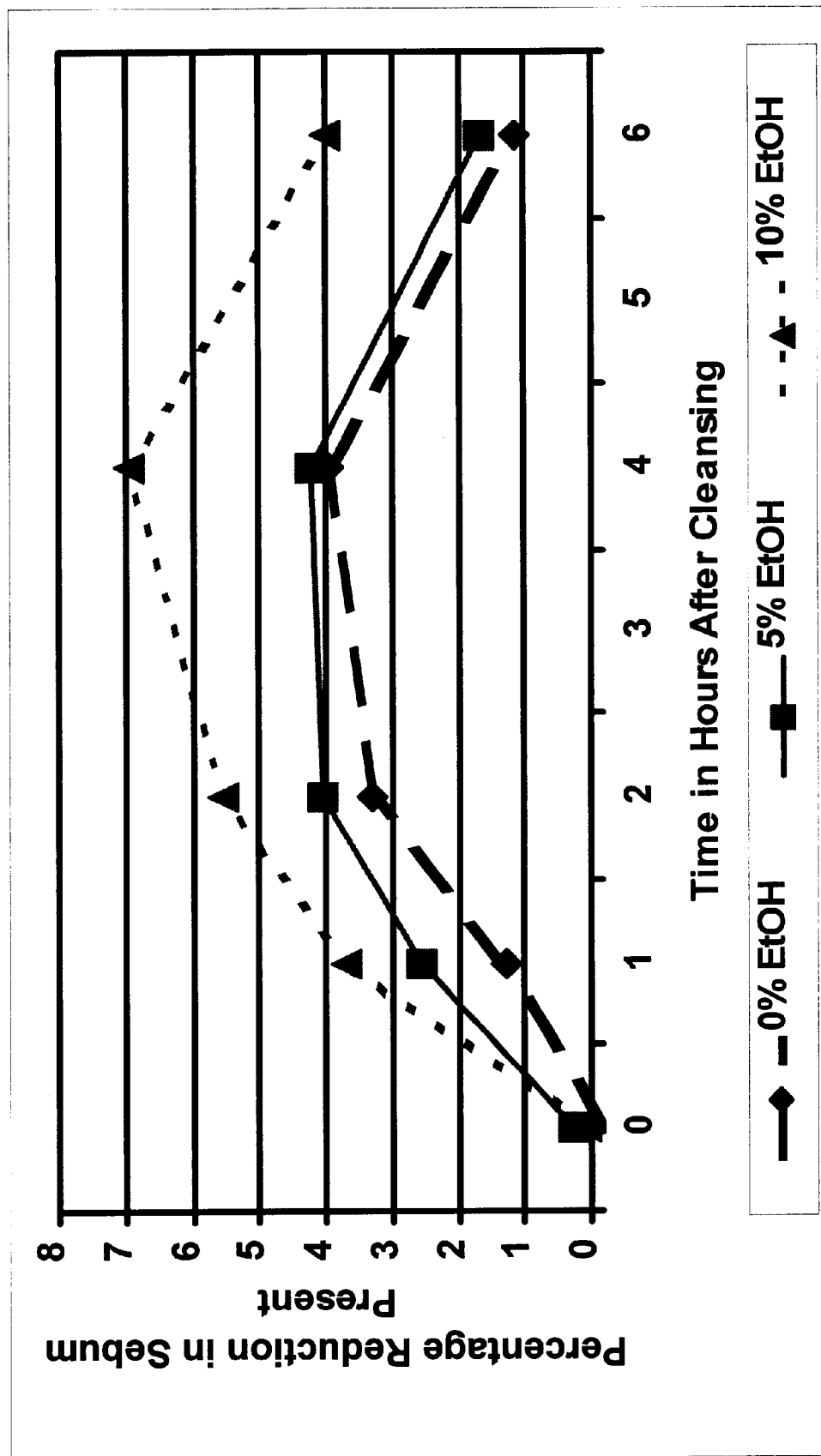
FIG. 1 is a graph demonstrating the effect of SD Alcohol 40B on the level of sebum present on the skin. The results are expressed as the difference in percent between treated and untreated skin prior to cleansing. The results are expressed as the percentage reduction in sebum present at each time point.

The following definitions and methods are provided to better define the present invention, and to guide those of ordinary skill in the art in the practice of the present invention. It must be noted that as used herein and in the appended claims, the singular forms "a", "an", and "the" include plural referents unless the context clearly dictates otherwise. Thus, for example, reference to "an alcohol" includes a plurality of such alcohols and reference to "the zinc salt" includes reference to one or more zinc salts and equivalents thereof known to those skilled in the art, and so forth.

Unless defined otherwise, all technical and scientific terms used herein have the same meaning as commonly understood to one of ordinary skill in the art to which this invention belongs.

Definitions

Alcohol: R—OH, wherein R is alkyl, especially lower alkyl (for example in methyl, ethyl or propyl alcohol). An alcohol may be either linear or branched, such as isopropyl alcohol.

Alkyl: A cyclic, branched, or straight chain alkyl group containing only carbon and hydrogen, and unless otherwise mentioned contains one to twelve carbon atoms. This term is further exemplified by groups such as methyl, ethyl, n-propyl, isobutyl, t-butyl, pentyl, pivalyl, heptyl, adamantyl, and cyclopentyl. Alkyl groups can either be unsubstituted or substituted with one or more substituents, e.g. halogen, alkyl, alkoxy, alkylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality.

Animal: Living multi-cellular vertebrate organisms, a category that includes, for example, mammals and birds. The term mammal includes both human and non-human mammals. Similarly, the term "subject" includes both human and veterinary subjects.

Hydroxyl: —OH.

Known or recognized compounds: Those that have previously been reported in patents or publications, or that otherwise qualify as prior art.

Mammal: This term includes both human and non-human mammals. Similarly, the term "subject" includes both human and veterinary subjects.

Reduction: Any decrease in a given parameter. For example, a reduction in the amount of sebum on the surface of the skin is a decrease in the amount of sebum on the skin. Any percentage decrease in sebum on the skin can be a reduction, so long as the decrease is significant, as measured by a statistical test for significance. In one specific, non-limiting example, a two-tailed test for significance is utilized. One of skill in art will readily be able to determine an appropriate statistical test for data comparison (e.g. two-tailed test, student's T text, Mann-Whitney test, etc.) in order to detect a reduction in a given parameter.

Sebum: A fatty exudate of the sebaceous glands, varying in consistency at different areas of the body. The primary components of sebum are fat and cellular debris.

Short chain alcohol: A cyclic, branched or straight chain alcohol of one to eight carbon atoms. This term is further exemplified by such alcohols as methyl, ethyl, isopropyl, butyl, and hexyl alcohols.

Vitamin $B_6$: Pyridoxine hydrochloride or a salt or derivative thereof. Specific, non-limiting examples of a salt or derivative of pyridoxine hydrochloride are Pyridoxine Hydronitrate, Pyridoxine Hydroacetate, or Pyridoxine amide.

Zinc Salt: A molecule that dissociates to release a zinc ion. Specific non-limiting examples of zinc salts are zinc gluconate, zinc nitrate, zinc chloride, and zinc acetate.

Without further elaboration, it is believed that one skilled in the art can, using this description and the specific examples described below, utilize the present invention to its fullest extent. The following examples are illustrative only, and not limiting of the remainder of the disclosure in any way whatsoever.

SPECIFIC EXAMPLES

Example 1

Methods for Evaluating Products Capable of Reducing Sebum on the Skin

As reviewed by Ayres, there are a variety of methods published through which products can be evaluated for their ability to reduce sebum output (Ayres, J. D. In Aust, L. B., ed. Cosmetic Claims Substantiation, Cosmetic Science and Technology Series, Volume 18. New York: Marcel Dekker, 1998:115–130). The most accurate and effective means of measuring the amount of sebum on the surface of the skin is through the use of Sebutape (Kligman, A. M. In: Montagna, W., Ellis, R. A., and Silver, A. F., eds. Advances in Biology of Skin:The Sebaceous Glands, Oxford, England: Pergamon Press, 1963: 110–124; Agache, P. G. In:Zviak, C., ed. The Science of Hair Care. New York: Marcel Dekker, 1986: 469–500; Ayres, J. D. In: Aust, L. B., ed. Cosmetic Claims Substantiation, Cosmetic Science and Technology Series, Volume 18. New York: Marcel Dekker, 1998:115–130). Sebutape is a microporous, hydrophobic, self-adhering polymeric film composed of many tiny air cavities. When this film comes in contact with sebum, it absorbs the sebum, displacing the air in the microcavities. The semi-transparent polymer film becomes transparent to light upon absorption of the sebum. Therefore, the Sebutape can be used not only to visualize the follicular pattern of sebaceous glands on the skin, but more importantly, the degree of transparency of the film has been found to be directly related to the amount of sebum on the skin. By measuring the degree of transparency using a spectrophotometer and visual light, the amount of sebum on the surface of the skin can be quantified. A modification of that method described by Ayres has been used to assess the efficacy of a series of formulations as described below.

Test subjects are brought into an environmentally controlled room and allowed to relax for a period of 15 to 30 minutes. On the first day of the test, the amount of sebum on each side of the forehead is then assessed using Sebutape (CuDerm Corporation, Dallas, Tex.) by pressing the tape to the skin for a period of 5 seconds. This period of time is sufficient to obtain accurate and reproducible measurements. The tape is visually evaluated to determine if there is a sufficient amount of transparency to make spectrophotometric measurements. If there is little or no transparency present, the subject is automatically disqualified from the test procedure.

The tape is then adhered to a clean plastic sheet and allowed to stand undisturbed for at least one hour. This allows the transparency of the tape to reach maximal values. The amount of sebum present on the tapes is then quantified using a spectrophotometer, such as a Hunter Lab Ultra Scan Spectrophotometer (Hunter Lab, Reston, Va.), by measuring the whiteness index (WI E313 (2/C) mode) as compared to a piece of virgin Sebutape. The resulting whiteness index values for each side of the forehead is then evaluated statistically. It should be noted that a high value in a whiteness index indicates a low presence of sebum on the skin. Thus, any increase in the presence of sebum on the skin results in a decrease in the corresponding whiteness index value. Subjects who exhibit statistically greater amounts on one side of the forehead relative to the other side of the forehead are disqualified from being subjects in this test.

On the next morning, the subjects are again brought into an environmentally controlled room and allowed to relax for a period of 15 to 30 minutes. The amount of sebum present on the skin of each qualified subject is again assessed using Sebutape. Following this sampling, the entire forehead of each qualified test subject is cleansed with 5 milliliters of a 10% solution of liquid skin cleanser in water applied to a clean paper towel and wiped across the forehead twice. The cleansed forehead is then rinsed by wiping it with a water soaked paper towel. This rinsing procedure is repeated two more times to ensure complete removal of the cleanser. Finally, the skin is gently patted dry with a fresh paper towel. After allowing the skin to equilibrate with the environmental conditions for 5 minutes, the amount of sebum present on each side of the forehead is measured using Sebutape. If these tapes exhibit a significant amount of sebum as assessed by a visual evaluation of the Sebutape following this cleansing process, the cleansing process is repeated as described above. If the Sebutape exhibits a significant amount of sebum after repeating the washing process, the test subject is disqualified.

Once the skin is determined to be clean as assessed by visual evaluation of the Sebutape, the test formulation is applied with a finger covered by a finger cot that is saturated with the test formulation to a single side of the forehead on a randomly determined manner. The treatment area is sufficient to allow for four independent Sebutape test sites within the test product applied area. The untreated side of the forehead is used as a control.

The test product is allowed to remain on the skin undisturbed for a period of one hour. At the end of this period of time, Sebutape measurements are made on both sides of the forehead (treated and untreated). Sebutape measurements are also made of the treated and untreated sides of the forehead of the test subject two hours after product application and at 2 hour intervals out to the conclusion of the test at 6 hours. In each case, the Sebutape is applied to a skin in a previously undisturbed area within the test site of the forehead for 5 seconds using constant pressure within the treated an untreated test sites.

Each Sebutape sample was kept at room temperature for at least one hour prior to spectrophotometric measurement in order to maximize its transparency. However, all Sebutape samples were spectrophotometrically analyzed within 24 hours after application to the skin of the test subjects, as the transparency of the Sebutape can start to fade after periods of time longer than 24 hours.

The Whiteness Index values are compared statistically using both a normal hypothesis analysis and a matched pairs analysis employing a Student t-Test at a 95% confidence limit in order to demonstrate the effectiveness of the treatment. In each case, the values for the test product treated site are compared to the baseline values (either from first day readings or from readings taken after cleansing the skin and before test product application). The same statistical analysis is conducted on the percentage change from baseline values using both the first day readings and the readings obtained after cleansing the skin but before applying the test product as the baseline values.

Example 2

Results of Initial Testing: A Complete Formulation

The formula for a test product used in this procedure described in Example 1 is shown below in Table 1.

TABLE 1

Formulation Tested

| Ingredient | Percentage (w/w)[a] |
|---|---|
| Water | 76.7990 |
| Anhydrous Ethyl Alcohol | 10.0000 |
| Cyclodextrin and Tea Tree Oil | 5.0000 |
| Polysorbate 20 | 3.0000 |
| Xanthan Gum | 1.0000 |
| Triethanolamine, 99% | 0.6500 |
| Leptospermum Scoparium Oil | 0.2500 |
| Coco Phosphatidyl PG-Dimonium Chloride | 0.5000 |
| Salicylic Acid | 0.5000 |
| Zinc Gluconate | 0.5000 |
| Galactoarabinan | 0.5000 |
| Tocopheryl Acetate | 0.2500 |
| Dipotassium Glycyrrhizinate | 0.2000 |
| DL Panthenol—50% in Water | 0.2000 |
| Cetearl Octanoate | 0.1000 |
| Titanium Dioxide | 0.1000 |
| Disodium EDTA | 0.1000 |
| Butylene Glycol, Water, and Watercress Extract | 0.1000 |
| Pyridoxine Hydrochloride | 0.0500 |
| Retinyl Palmitate and Tocopherol | 0.0010 |
| Butylene Glycol, Water, and Burdock Extract | 0.1000 |
| Aloe Barbadensis Leaf Juice | 0.1000 |
| Total | 100.0000 |

[a]Percentage by weight.

Sebum on the untreated skin of the test subjects was measured with Sebutape on Day 1. The pooled test results for the treated (average 73.22±3.296, range 70.42–78.04) ) and untreated (73.51±2.846, range 70.05–77.19) sites prior to cleansing are not statistically different at the 95% confidence interval. A matched-pairs evaluation of these same results was also conducted. The results were not statistically different as determined by this statistical evaluation method. This data demonstrates that for each test subject, the two sides of the forehead had the same amount of sebum present, and thus no bias is inherently present prior to the application of the test formulation.

An experiment was then conducted in which the test formulation (see Table 1) was applied to the treatment site on the forehead. The presence of sebum was measured initially, and 1, 2, 4, and 6 hours after the application of the test formulation for both test sites, the site treated with the test formulation and the untreated site. The initial sebum measurement (after through cleansing of the forehead) demonstrated that there was very little sebum present on either the treatment or the control side of the forehead initially. In addition, no difference was found in the amount of sebum on the "treatment" site (84.9±1.202) as compared to the "untreated" site (85.15±0.846) prior to the application of the test agent.

However, the side of the forehead treated with the test product exhibits a lower amount of surface sebum at one hour (an average of 84.28±1.202 for the treated versus an average of 81.42±1.298 for the untreated), two hours (an average of 82.2±1.224 for the treated side versus 79.40±1.695 for the untreated side), four hours (an average of 80.35±1.526 for the treated side versus an average of 75.57±2.145 for the untreated side), and six hours (an average of 76.41±2.563 for the treated side versus an average of 73.85±2.187) for the untreated side), following application of the test product. This difference is statistically significant at the 95% confidence level at each of these evaluation points. However, this difference between the treated and untreated sites is not statistically significantly different immediately following the cleansing process and prior to the application of the test product (that is, immediately after cleansing). These statistical results are also found when the matched-pairs statistical technique is used to evaluate the data as shown in Table 2.

TABLE 2

Statistical Evaluation of Sebutape Readings of Skin Treated with Test Formula Versus Cleansed Skin Not Treated With the Test Formula by a Matched Pairs Technique[a]

| Subject No. | Initial Reading[b] | After Cleansing Reading | 1 Hour Reading | 2 Hour Reading | 4 Hour Reading | 6 Hour Reading |
|---|---|---|---|---|---|---|
| 1 | 1.55 | −0.13 | 2.93 | 5.24 | 6.67 | 4.27 |
| 2 | 1.04 | −0.21 | NRT[c] | 4.48 | 4.90 | 2.84 |
| 3 | 0.81 | −0.05 | 1.84 | 2.70 | 2.46 | 2.61 |
| 4 | −1.85 | −1.34 | 1.12 | 3.08 | 5.02 | 0.87 |
| 5 | −1.47 | −0.15 | 1.94 | 2.15 | 4.43 | 2.51 |
| 6 | 0.61 | −0.55 | 0.93 | 2.94 | 4.04 | 2.45 |
| 7 | −1.47 | 0.43 | 3.68 | 5.24 | 5.57 | 2.93 |
| 8 | −0.34 | 0.04 | 2.76 | 4.57 | 3.52 | 2.00 |
| Average | −0.29 | −0.24 | 2.17 | 3.80 | 4.58 | 2.56 |
| Std. Dev. | 1.292 | 0.520 | 1.001 | 1.218 | 1.286 | 0.951 |
| $t_c$[d] | 0.635 | 1.305 | 6.132 | 8.824 | 10.073 | 7.614 |
| Stat. Diff.[e] | No | No | Yes | Yes | Yes | Yes |

[a]The matched pair in each case is calculated from the formula:
Value = Value for Treated Site$_t$ − Valued for Untreated Site$_t$
[b]Reading taken after cleansing both sites with a skin cleanser as described in test methodology.
[c]NRT—No reading taken because of subject unavailability
[d]Calculated statistical Student t value.
[e]Statistical difference at the 95% confidence interval using a 2-tailed test.

The results clearly demonstrate that application of the test formulation results in decreased amounts of sebum being present on the skin at 1, 2, 4, and 6 hours after treatment.

The spectrophotometrically measured amounts of sebum on the skin were calculated as the percentage difference between the freshly cleansed skin and other evaluation points. In this method of evaluation, the differences between the treated and untreated sites are not statistically different for the initial evaluation. However, after the test product has been applied to the treatment sites, the results are statistically different at the 95% confidence level for each evaluation point (1, 2, 4 and 6 hours after product application). When this same data is evaluated using a matched-pairs statistical technique, as shown in Table 3, the same statistical significance between data points was found.

TABLE 3

Statistical Evaluation of Sebutape Percentage Difference Readings[a] from Baseline (After Cleansing) of Skin Treated with Test Formula Versus Cleansed Skin Not Treated With the Test Formula Using a Matched Pairs Technique[b]

| Subject No. | Initial Reading[c] | 1 Hour Reading | 2 Hour Reading | 4 Hour Reading | 6 Hour Reading |
|---|---|---|---|---|---|
| 1 | 1.93 | 3.55 | 6.23 | 7.89 | 5.09 |
| 2 | 1.43 | NRT[d] | 5.49 | 5.98 | 3.55 |
| 3 | 1.00 | 2.21 | 3.21 | 2.93 | 3.11 |
| 4 | −0.88 | 2.94 | 5.27 | 7.53 | 2.44 |
| 5 | −1.57 | 2.43 | 2.67 | 5.32 | 3.08 |
| 6 | −0.13 | 1.73 | 4.08 | 5.36 | 3.47 |
| 7 | −2.17 | 3.85 | 5.70 | 6.11 | 3.01 |
| 8 | −0.44 | 3.20 | 5.34 | 4.10 | 2.31 |
| Average | −0.05 | 2.79 | 4.67 | 5.87 | 3.39 |
| Std. Dev. | 1.564 | 0.813 | 1.354 | 1.639 | 0.833 |
| $T_c^e$ | 0.0904 | 9.706 | 9.755 | 10.130 | 11.511 |
| Stat. Diff.[f] | No | Yes | Yes | Yes | Yes |

[a]The percentage difference is calculated from the formulas:
Treated Site Percentage Difference = $100*[((\text{Treated Site}_{\text{After Cleansing}} - \text{Treated Site}_t)/\text{Treated Site}_{\text{After Cleansing}})]$
Untreated Site Percentage Difference = $100*[((\text{Untreated Site}_{\text{After Cleansing}} - \text{Untreated Site}_t)/\text{Untreated Site}_{\text{After Cleansing}})]$
[b]The matched pair in each case is calculated from the formula:
Value = Value for Treated Site$_t$ − Valued for Untreated Site$_t$
[c]Reading taken before cleansing both sites with a skin cleanser as described in test methodology.
[d]NRT—No reading taken because of subject unavailability
[e]Calculated statistical Student t value.
[f]Statistical difference at the 95% confidence interval using a 2-tailed test.

The percentage difference in the freshly cleansed skin of the treatment site and the freshly cleansed skin of the control site are not statistically different. However, the percentage difference between the treated and untreated sites is statistically different at each subsequent evaluation point. These same results are found when the data is evaluated using a matched-pairs statistical technique as shown in Table 4.

TABLE 4

Statistical Evaluation of Sebutape Percentage Difference Readings[a] from Baseline (Before Cleansing) of Skin Treated with Test Formula Versus Skin Not Treated With the Test Formula Using a Matched Pairs Technique[b]

| Subject No. | Initial Reading[c] | 1 Hour Reading | 2 Hour Reading | 4 Hour Reading | 6 Hour Reading |
|---|---|---|---|---|---|
| 1 | −2.48 | 1.55 | 4.88 | 7.01 | 3.73 |
| 2 | −1.89 | NRT[d] | 4.50 | 5.13 | 2.39 |
| 3 | −1.19 | 1.24 | 2.35 | 2.07 | 2.29 |
| 4 | 1.24 | 4.72 | 7.46 | 10.10 | 3.97 |
| 5 | 2.21 | 5.05 | 5.28 | 8.34 | 5.58 |
| 6 | 0.16 | 2.08 | 4.68 | 6.08 | 3.98 |
| 7 | 2.99 | 7.42 | 9.52 | 9.89 | 6.15 |
| 8 | 0.60 | 4.33 | 6.80 | 5.34 | 3.23 |
| Average | 0.10 | 3.68 | 5.53 | 6.95 | 4.01 |
| Std. Dev. | 2.176 | 2.451 | 2.312 | 2.839 | 1.456 |
| $T_c^e$ | 0.130 | 4.247 | 6.765 | 6.924 | 7.790 |
| Stat. Diff.[f] | No | Yes | Yes | Yes | Yes |

[a]The percentage difference is calculated from the formulas:
Treated Site Percentage Difference $100*[((\text{Treated Site}_t - \text{Treated Site}_{\text{Before Cleansing}})/\text{Treated Site}_{\text{Before Cleansing}})]$
Untreated Site Percentage Difference $100*[((\text{Untreated Site}_t - \text{Untreated Site}_{\text{Before Cleansing}})/\text{Untreated Site}_{\text{Before Cleansing}})]$
[b]The matched pair in each case is calculated from the formula:
Value = Value for Treated Site$_t$ − Valued for Untreated Site$_t$
[c]Reading taken after cleansing both sites with a skin cleanser as described in test methodology.
[d]NRT—No reading taken because of subject unavailability
[e]Calculated statistical Student t value.
[f]Statistical difference at the 95% confidence interval using a 2-tailed test.

The percentage difference in the amounts of skin oils produced between the treated and untreated skin sites is as follows:

When compared to the untreated skin prior to being cleansed as expressed in terms of the amount of time following the application of the test product:
   1 Hour after application—3.68%
   2 Hours after application—5.53%
   4 Hours after application—6.95%
   6 Hours after application—4.01%

When compared to freshly cleansed skin (using the test product) as expressed in terms of the amount of time following application of the test product:
   1 Hour after application—2.79%
   2 Hours after application—4.67%
   4 Hours after application—5.87%
   6 Hours after application—3.39%

Based upon these results, it has been clearly demonstrated that the treatment of the skin with the test product is effective at reducing the appearance of surface skin oils. The test results reveal that this effect lasts for up to 6 hours following a single application of the product.

Example 3

Partial Formulation Compositions for Comparative Analysis

The active components of the formula listed in Table 1 are SD Alcohol 40-B (ethyl alcohol), Pyridoxine Hydrochloride (Vitamin $B_6$), and Zinc Gluconate. In order to demonstrate that these components have a definite effect upon the amount of sebum present on the skin, seven separate formulations were made up and tested in the test procedure described above. These partial formulations are listed in Table 5.

TABLE 5

Partial Formulations Tested

| | Percentage (w/w) of Formulas | | | | | | |
|---|---|---|---|---|---|---|---|
| Ingredients | A | B | C | D | E | F | G |
| Water | 81.7990 | 86.7990 | 76.8240 | 76.8490 | 77.0490 | 77.2990 | 82.0740 |
| Anhydrous Ethyl Alcohol | 5.0000 | — | 10.0000 | 10.0000 | 10.0000 | 10.0000 | 5.0000 |

TABLE 5-continued

Partial Formulations Tested

Percentage (w/w) of Formulas

| Ingredients | A | B | C | D | E | F | G |
|---|---|---|---|---|---|---|---|
| Cyclodextrin and Tea Tree Oil | 5.0000 | 5.0000 | 5.0000 | 5.0000 | 5.0000 | 5.0000 | 5.0000 |
| Polysorbate 20 | 3.0000 | 3.0000 | 3.0000 | 3.0000 | 3.0000 | 3.0000 | 3.0000 |
| Xanthan Gum | 1.0000 | 1.0000 | 1.0000 | 1.0000 | 1.0000 | 1.0000 | 1.0000 |
| Triethanolamine, 99% | 0.6500 | 0.6500 | 0.6500 | 0.6500 | 0.6500 | 0.6500 | 0.6500 |
| Leptspermum Scoparium Oil | 0.2500 | 0.2500 | 0.2500 | 0.2500 | 0.2500 | 0.2500 | 0.2500 |
| Coco Phosphatidyl PG-Dimonium Chloride | 0.5000 | 0.5000 | 0.5000 | 0.5000 | 0.5000 | 0.5000 | 0.5000 |
| Salicylic Acid | 0.5000 | 0.5000 | 0.5000 | 0.5000 | 0.5000 | 0.5000 | 0.5000 |
| Zinc Gluconate | 0.5000 | 0.5000 | 0.5000 | 0.5000 | 0.2500 | — | 0.2500 |
| Galactoarabinan | 0.5000 | 0.5000 | 0.5ooo | 0.5000 | 0.5000 | 0.5000 | 0.5000 |
| Tocopheryl Acetate | 0.2500 | 0.2500 | 0.2500 | 0.2500 | 0.2500 | 0.2500 | 0.2500 |
| Dipotassium Glycyrrhizinate | 0.2000 | 0.2000 | 0.2000 | 0.2000 | 0.2000 | 0.2000 | 0.2000 |
| DL Panthenol—50% in Water | 0.2000 | 0.2000 | 0.2000 | 0.2000 | 0.2000 | 0.2000 | 0.2000 |
| Cetearyl Octanoate | 0.1000 | 0.1000 | 0.1000 | 0.1000 | 0.1000 | 0.1000 | 0.1000 |
| Titanium Dioxide | 0.1000 | 0.1000 | 0.1000 | 0.1000 | 0.1000 | 0.1000 | 0.1000 |
| Disodium EDTA | 0.1000 | 0.1000 | 0.1000 | 0.1000 | 0.1000 | 0.1000 | 0.1000 |
| Butylene Glycol, Water, and Watercress Extract | 0.1000 | 0.1000 | 0.1000 | 0.1000 | 0.1000 | 0.1000 | 0.1000 |
| Pyridoxine Hydrochloride | 0.0500 | 0.0500 | 0.0250 | — | 0.0500 | 0.0500 | 0.0250 |
| Retinyl Palmitate and Tocopherol | 0.0010 | 0.0010 | 0.0010 | 0.0010 | 0.0010 | 0.0010 | 0.0010 |
| Butylene Glycol, Water, and Burdock Extract | 0.1000 | 0.1000 | 0.1000 | 0.1000 | 0.1000 | 0.1000 | 0.1000 |
| Aloe Barbadensis Leaf Juice | 0.1000 | 0.1000 | 0.1000 | 0.1000 | 0.1000 | 0.1000 | 0.1000 |
| Total | 100.0000 | 100.0000 | 100.0000 | 100.0000 | 100.0000 | 100.0000 | 100.0000 |

[a]Percentage by weight.

Example 4

Effect of SD Alcohol 40-B

The effect of the presence of the SD Alcohol 40-B on the effectiveness of the formulation was evaluated in formulations A and B of Table 5. Formula A contains half the amount of the alcohol contained in the original formula (see Table 1) whereas Formula B does not contain any of this alcohol.

An experiment was then conducted in which the test formulation A or B was applied to the treatment site on the forehead of the test subjects. The presence of sebum was measured initially, and 1, 2, 4, and 6 hours after the application of the test formulation for both test sites, the site treated with the test formulation and the untreated site. The initial sebum measurement (after thorough cleansing of the forehead) demonstrated that there was very little sebum present on either the treatment or the control side of the forehead initially. For each set of test subjects, there was no initial difference (before application of any formulation) in the amount of sebum on the "treatment" site as compared to the "untreated" site for either test series.

The side of the forehead treated with formula A exhibited a lower amount of surface sebum at 1 hour (an average whiteness value of 83.53±0.453 for the treated group as compared to an average whiteness value of 81.85±1.059 for the untreated group) and 2 hours (an average whiteness value of 82.19±0.596 for the treated group as compared to an average whiteness value of 79.43±1.500 for the untreated group) after treatment. The side of the forehead treated with formula B exhibited a lower amount of surface sebum at 1 hour (an average whiteness value of 84.19±0.397 for the treated group as compared to an average whiteness value of 82.75±0.864 for the untreated group), 2 hours (an average whiteness value of 82.85±0.627 for the treated group as compared to an average whiteness value of 79.83±1.641 for the untreated group), and 4 hours (an average whiteness value of 79.22±0.874 for the treated group as compared to an average whiteness value of 76.02±1.906 for the untreated group) after treatment. These differences are statistically significant at the 95% confidence level at each of these evaluation points.

However, this difference between the treated and untreated sites are not statistically significantly different at 6 hours for either sample or at 4 hours for the 5% alcohol formula (Formula A). They are also not statistically different immediately following the cleansing process or when measured the previous day. These same statistical results are found when the matched-pairs statistical technique is used to evaluate the data as shown in Tables 6 and 7, except that the 4 hour evaluation yields a statistically significant result for both test formulas.

TABLE 6

Statistical Evaluation of Sebutape Readings of Skin Treated with Test Formula Versus Cleansed Skin Not Treated With the Test Formula by a Matched Pairs Technique[a]
Formula A (5% SD Alcohol 40-B)

| Subject No. | Initial Reading[b] | After Cleansing Reading | 1 Hour Reading | 2 Hour Reading | 4 Hour Reading | 6 Hour Reading |
|---|---|---|---|---|---|---|
| 1 | −0.01 | 0.01 | 1.02 | 2.37 | 3.78 | 2.12 |
| 2 | −0.29 | −0.13 | 0.92 | 3.19 | 3.89 | 1.58 |
| 3 | −0.10 | −0.27 | 2.13 | 2.33 | 2.24 | 0.46 |
| 4 | −0.45 | 0.02 | 3.12 | 4.55 | 3.47 | 1.34 |
| 5 | −0.88 | 0.10 | 0.78 | 1.36 | 1.52 | −0.53 |
| 6 | 0.52 | 0.01 | 2.11 | 2.73 | 2.54 | 1.15 |
| Average | −0.20 | −0.04 | 1.68 | 2.76 | 2.91 | 1.02 |
| Std. Dev. | −0.469 | 0.134 | 0.926 | 1.066 | 0.954 | 0.934 |
| $t_c$[c] | 1.045 | 0.731 | 4.444 | 6.342 | 7.472 | 2.675 |
| Stat. Diff.[d] | No | No | Yes | Yes | Yes | Yes |

[a]The matched pair in each case is calculated from the formula:
Value = Value for Treated Site$_t$ − Valued for Untreated Site$_t$
[b]Reading taken after cleansing both sites with a skin cleanser as described in test methodology.
[c]Calculated statistical Student t value.
[d]Statistical difference at the 95% confidence interval using a 2-tailed test.

TABLE 7

Statistical Evaluation of Sebutape Readings of Skin Treated with Test Formula Versus Cleansed Skin Not Treated With the Test Formula by a Matched Pairs Technique[a]
Formula B (0% SD Alcohol 40-B)

| Subject No. | Initial Reading[b] | After Cleansing Reading | 1 Hour Reading | 2 Hour Reading | 4 Hour Reading | 6 Hour Reading |
|---|---|---|---|---|---|---|
| 1 | −0.01 | −0.04 | 0.94 | 2.77 | 4.81 | 3.25 |
| 2 | 0.91 | 0.09 | 1.43 | 3.86 | 4.57 | 1.69 |
| 3 | −0.03 | −0.10 | 1.07 | 2.66 | 2.63 | −0.52 |
| 4 | −0.07 | −0.35 | 1.11 | 2.75 | 2.30 | 0.62 |
| 5 | −0.88 | −0.08 | 0.67 | 1.37 | 0.95 | −0.44 |
| 6 | 0.55 | 0.16 | 1.09 | 1.71 | 2.75 | 0.86 |
| Average | 0.08 | −0.05 | 1.05 | 2.52 | 3.00 | 0.91 |
| Std. Dev. | 0.612 | 0.177 | 0.248 | 0.884 | 1.458 | 1.417 |
| $t_c$[c] | 0.320 | 0.692 | 10.371 | 6.983 | 5.057 | 1.573 |
| Stat. Diff.[d] | No | No | Yes | Yes | Yes | No |

[a]The matched pair in each case is calculated from the formula:
Value = Value for Treated Site$_t$ − Valued for Untreated Site$_t$
[b]Reading taken after cleansing both sites with a skin cleanser as described in test methodology.
[c]Calculated statistical Student t value.
[d]Statistical difference at the 95% confidence interval using a 2-tailed test.

The spectrophotometrically measured amounts of sebum were then calculated as the percentage difference between the freshly cleansed skin and other evaluation points. In this method of evaluation, the differences between the treated and untreated sites for either Formulas A and B are not statistically different for the initial evaluation (Day 1 results) or at the 6 hour evaluation. However, after the test product has been applied to the treatment sites, the results are statistically different at the 95% confidence level at the 1, 2, and 4 hour evaluation points. When these same results are evaluated using a matched-pairs statistical technique, the same statistically significance between data points are found, except for the fact that Formula A becomes statistically significant at 6 hours, which was not previously found.

The percentage difference results between the initial (Day 1) results and the data at the other evaluation points for Formulas A and B were further evaluated. The statistical evaluation of this data revealed the same outcome as found previously for the percentage difference from the freshly cleansed and treated skin described above. The percentage difference in the freshly cleansed treatment and control sites were not statistically different. In addition, the results at the 6 hour evaluation point were not statistically significant. However, the percentage difference between the treated and untreated sites is statistically different at 1, 2, and 4 hours following the application of either of these two test formulas (Formulas A and B). These same results are found when the data is evaluated using a matched-pairs statistical technique.

The percentage difference in the amounts of skin oils produced between the Treated and untreated skin sites is as follows:

When compared to the untreated skin prior to being cleansed as expressed in terms of the amount of time following the application of the test product:

|  | Formula B (0% Alcohol) | Formula A (5% Alcohol) |
|---|---|---|
| 1 Hour after application | 1.29% | 2.57% |
| 2 Hours after application | 3.29% | 4.03% |
| 4 Hours after application | 3.96% | 4.23% |
| 6 Hours after application | 1.14% | 1.67% |

These results are shown graphically in FIG. 1.

When compared to freshly cleansed skin (using the test product) as expressed in terms of the amount of time following application of the test product:

|  | Formula B (0% Alcohol) | Formula A (5% Alcohol) |
|---|---|---|
| 1 Hour after application | 1.30% | 2.04% |
| 2 Hours after application | 3.01% | 3.32% |
| 4 Hours after application | 3.58% | 3.49% |
| 6 Hours after application | 1.45% | 1.26% |

Figure 2:
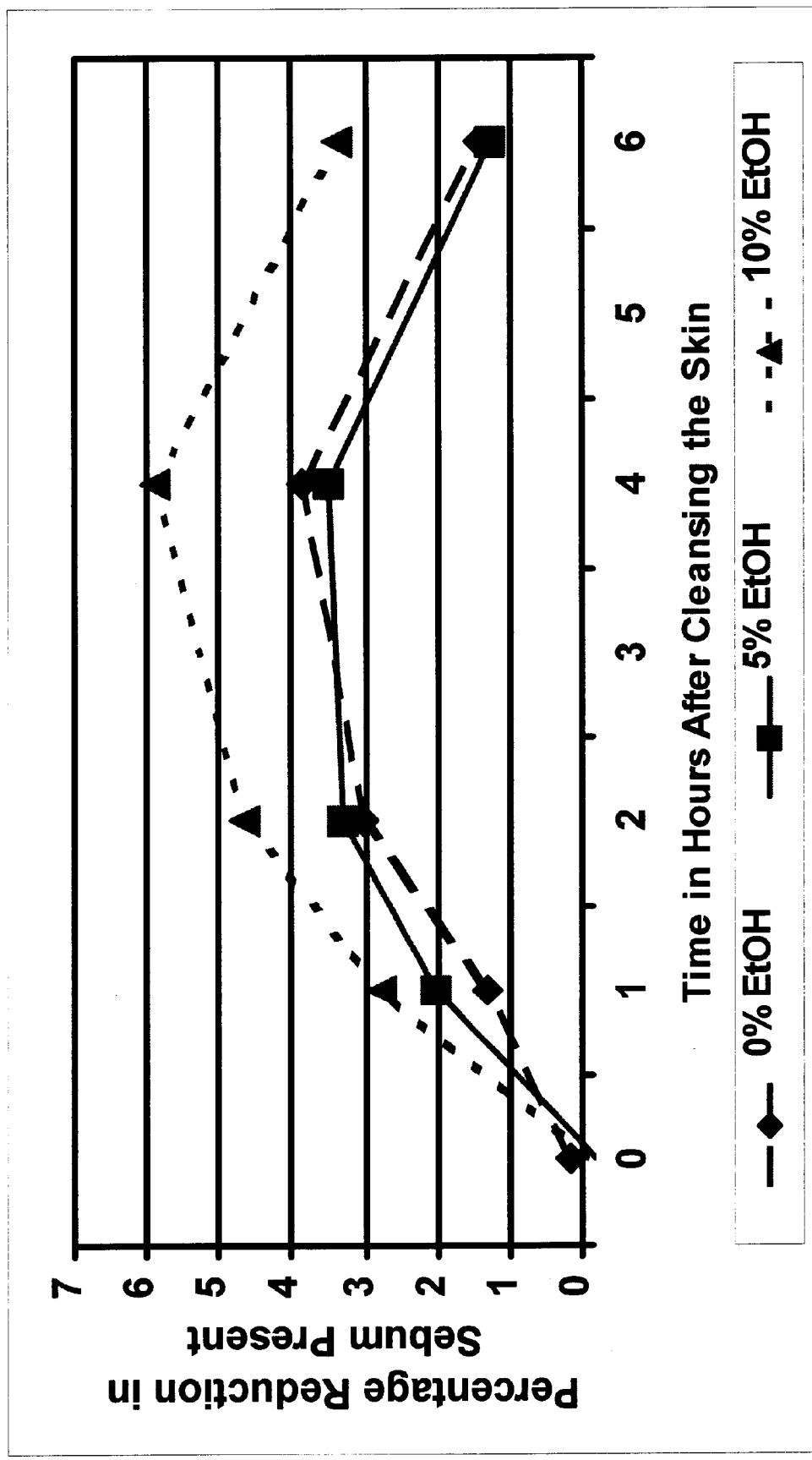
FIG. 2 is a second graph demonstrating the effect of SD Alcohol 40B on the level of sebum present on freshly cleansed skin. The results are expressed as the difference in percent between treated and untreated skin after cleansing. The results are expressed as the percentage reduction in sebum present at each time point.

These results are graphically shown in FIG. 2.

These results clearly demonstrate that the treatment of the skin with the test formulations containing either 0% or 5% SD Alcohol 40-B are effective at reducing the appearance of surface skin oils. However, neither of these formulations are as effective as the combination containing 10% SD Alcohol 40-B (the formulation shown in Table 1). The test results reveal that the effectiveness of Formulas A (5% alcohol) and B (0% alcohol) last for up to 6 hours following a single application of the product.

A careful evaluation of the results as shown in FIGS. 1 and 2 clearly indicate that the 10% SD Alcohol 40-B formula exhibits synergy that is unexpected. This is evidenced by the fact that the graph for the formulation containing 10% alcohol is more effective at 4 and 6 hours than the other formulas evaluated. Furthermore, given the data listed above, the effectiveness expected from the 10% alcohol formulation is more the difference in the 0 and 5% alcohol containing formulations. The following data demonstrates that difference.

| Percentage Reduction in Sebum | | | |
|---|---|---|---|
| Evaluation Time | Theoretical[a] | Actual | Difference |
| For Results Obtained Before Cleansing the Skin | | | |
| 1 hour | 3.85% | 3.68% | −0.17% |
| 2 hours | 4.77% | 5.53% | 0.76% |
| 3 hours | 4.50% | 6.95% | 2.45% |
| 4 hours | 2.20% | 4.01% | 1.81% |
| For Results Obtained from Freshly Cleansed Skin | | | |
| 1 hour | 2.78% | 2.79% | 0.01% |
| 2 hours | 3.63% | 4.67% | 1.04% |
| 3 hours | 3.58% | 5.87% | 2.29% |
| 4 hours | 1.45% | 3.39% | 1.94% |

[a]Calculated from the difference between the 0% and 5% SD Alcohol 40-B formulations, corrected for the additional 5% alcohol and then added to the baseline value assumed to be the 0% SD Alcohol 40-B value.

Example 5

Effect of Pyridoxine Hydrochloride (Vitamin $B_6$)

The effect of the presence of the Vitamin $B_6$ on the effectiveness of the formulation was evaluated in formulations C and D of Table 5. Formula C contains half the amount of the Vitamin $B_6$ contained in the original formula (see Table 1) whereas Formula B does not contain any Vitamin $B_6$.

The results of the Day 1 comparison between the spectrophotometrically measured amounts of sebum present on untreated, uncleansed skin as measured with Sebutape on the forehead of the test subjects using these formulations and revealed that the average values for the treated and untreated sites prior to cleansing were not statistically different at the 95% confidence interval. The matched-pairs evaluation of these same results also demonstrated that there was no statistically significant difference.

The effects of the amount of Vitamin $B_6$ (pyridoxine hydrochloride) were demonstrated using spectrophotometric measurements of the amount of sebum on the surface of the skin. The data clearly shows that the side of the forehead treated with these test formulation C (with 0.025% Vitamin $B_6$) exhibit a lower amount of surface sebum at 1 hour (an average whiteness value of 83.08±0.488 for the treated group as compared to an average whiteness value of 81.30±0.454 for the untreated group), 2 hours (an average whiteness value of 81.23±1.229 for the treated group as compared to an average whiteness value of 77.98±1.252 for the untreated group), and four hours an (average whiteness value of 75.99±0.826 for the treated group as compared to an average whiteness value of 74.37±1.542 for the untreated group) after treatment (statistical difference at the 95% confidence interval using the 2-tailed test). The side of the forehead treated with test formulation D exhibit a lower amount of surface sebum at 1 hour (an average whiteness value of 83.64±0.205 for the treated group as compared to an average whiteness value of 82.67±0.360 for the untreated group) and 2 hours (an average whiteness value of 81.75±0.0.288 for the treated group as compared to an average whiteness value of 79.86±0.710 for the untreated group) after treatment (statistical difference at the 95% confidence interval using the 2-tailed test).

As described above, these differences are statistically significant at the 95% confidence level at each of these evaluation points. However, the difference between the treated and untreated sites was not statistically significantly different at 6 hours for either sample or at 4 hours for the 0% Vitamin $B_6$ formula (Formula D). The data were also not statistically different immediately following the cleansing process or when measured the previous day.

A somewhat different picture is obtained when the results for these formulations are evaluated by a matched-pairs statistical technique as shown in Tables 8 and 9.

TABLE 8

Statistical Evaluation of Sebutape Readings of Skin Treated with Test Formula Versus Cleansed Skin Not Treated With the Test Formula by a Matched Pairs Technique[a]
Formula C (0.025% Pyridoxine Hydrochloride (Vitamin $B_6$))

| Subject No. | Initial Reading[b] | After Cleansing Reading | 1 Hour Reading | 2 Hour Reading | 4 Hour Reading | 6 Hour Reading |
|---|---|---|---|---|---|---|
| 1 | 0.09 | −0.06 | 1.18 | 1.88 | 1.35 | 0.31 |
| 2 | 0.03 | 0.15 | 2.13 | 3.81 | 2.43 | 0.35 |
| 3 | −0.12 | 0.16 | 1.82 | 3.47 | 2.30 | NR[c] |
| 4 | 0.17 | 0.07 | 1.65 | 3.80 | 2.31 | 0.31 |
| 5 | 0.04 | 0.05 | 2.18 | 4.11 | 1.17 | 0.65 |
| 6 | −0.04 | 0.12 | 1.75 | 2.46 | 0.17 | 0.31 |
| Average | 0.01 | 0.08 | 1.79 | 3.26 | 1.62 | 0.39 |
| Std. Dev. | 0.121 | 0.082 | 0.364 | 0.884 | 0.891 | 0.149 |
| $t_c$[d] | 0.202 | 2.390 | 12.046 | 9.033 | 4.454 | 5.853 |
| Stat. Diff.[e] | No | No | Yes | Yes | Yes | Yes |

[a]The matched pair in each case is calculated from the formula:
Value = Value for Treated Site$_t$ − Valued for Untreated Site$_t$
[b]Reading taken after cleansing both sites with a skin cleanser as described in test methodology.
[c]NR—No reading taken because of subject unavailability
[d]Calculated statistical Student t value.
[e]Statistical difference at the 95% confidence interval using a 2-tailed test.

TABLE 9

Statistical Evaluation of Sebutape Readings of Skin Treated with Test Formula Versus Cleansed Skin Not Treated With the Test Formula by a Matched Pairs Technique[a]
Formula D (0% Pyridoxine Hydrochloride (Vitamin $B_6$))

| Subject No. | Initial Reading[b] | After Cleansing Reading | 1 Hour Reading | 2 Hour Reading | 4 Hour Reading | 6 Hour Reading |
|---|---|---|---|---|---|---|
| 1 | −0.17 | −0.14 | 0.77 | 2.68 | 1.40 | −0.22 |
| 2 | 0.08 | −0.10 | 0.98 | 1.74 | 0.18 | −0.02 |
| 3 | 0.20 | 0.30 | 0.97 | 1.47 | 0.21 | −0.26 |
| 4 | −0.23 | 0.06 | 0.68 | 1.23 | 0.64 | 0.00 |
| 5 | 0.18 | 0.13 | 1.44 | 2.33 | 1.40 | 0.08 |
| Average | 0.01 | 0.05 | 0.97 | 1.89 | 0.77 | −0.08 |
| Std. Dev. | 0.200 | 0.179 | 0.294 | 0.603 | 0.607 | 0.148 |
| $t_c$[c] | 0.112 | 0.625 | 7.378 | 7.009 | 2.837 | 1.209 |
| Stat. Diff.[d] | No | No | Yes | Yes | Yes | No |

[a]The matched pair in each case is calculated from the formula:
Value = Value for Treated Site$_t$ − Valued for Untreated Site$_t$
[b]Reading taken after cleansing both sites with a skin cleanser as described in test methodology.
[c]Calculated statistical Student t value.
[d]Statistical difference at the 95% confidence interval using a 2-tailed test.

Using this powerful statistical technique, the results for both formulas become statically significant at 1, 2, and 4 hours. The results for Formula C (0.025% Vitamin $B_6$) also becomes significant at 6 hours. The remaining results are not statistically significant. Given the power to discern a smaller level of differences using matched pairs statistical methods, the differences found using this technique are not only real, but also important.

The spectrophotometrically measured amounts of sebum were then calculated as the percentage difference between the freshly cleansed skin and other evaluation points. In this method of evaluation, the differences between the treated and untreated sites for either Formulas C and D are not statistically different for the initial evaluation (Day 1 results) or at the 6 hour evaluation. However, after the test product has been applied to the treatment sites, the results are statistically different at the 95% confidence level at 1 and 2 hours for both formulas as well as at the 4 hours evaluation point for Formula C (0.025% Vitamin $B_6$).

Again a somewhat different picture is obtained when the results for these formulations are evaluated by a matched-pairs statistical technique. Using this powerful statistical technique, the results for both formulas become statistically significant (2-tailed test) at 1 and 2 hours. The results for Formula C (0.025% Vitamin $B_6$) also becomes significant at 4 and 6 hours. The remaining results are not statistically significant. Given the power to discern a smaller level of differences using matched pairs statistical methods, the results again demonstrate that the differences found are not only real, but also important.

The percentage difference results between the initial (Day 1) results and the data at the other evaluation points for Formulas C and D was further evaluated. The statistical evaluation of this data revealed the same outcome as found previously for the percentage difference from the freshly cleansed and treated skin. Briefly, the percentage difference in the freshly cleansed treatment and control site are not statistically different (2-tailed test). The results at the 6 hour evaluation point were not statistically significant either. Additionally, the results for Formula D at 4 hours is not statistically significant. However, the percentage difference between the treated and untreated sites was statistically different at 1 and 2 hours following the application of either of these two test formulas (Formulas C and D) as well as at 4 hours for Formula C (0.025% Vitamin $B_6$). These same results are found when the data is evaluated using a matched-pairs statistical technique as shown in Table 10 and 11, except that the result for the 6 hour evaluation point becomes statistically significant using this technique.

TABLE 10

Statistical Evaluation of Sebutape Percentage Difference Readings[a] from Baseline (Before Cleansing) of Skin Treated with Test Formula Versus Skin Not Treated With the Test Formula Using a Matched Pairs Technique[b]
Formula C (0.025% Pyridoxine Hydrochloride (Vitamin $B_6$))

| Subject No. | Initial Reading[c] | 1 Hour Reading | 2 Hour Reading | 4 Hour Reading | 6 Hour Reading |
|---|---|---|---|---|---|
| 1 | −0.23 | 1.51 | 2.49 | 1.76 | 0.31 |
| 2 | 0.16 | 2.95 | 5.31 | 3.38 | 0.45 |
| 3 | 0.42 | 2.73 | 5.03 | 3.39 | NR[d] |
| 4 | −0.19 | 2.05 | 5.09 | 3.00 | 0.20 |
| 5 | 0.01 | 2.92 | 5.57 | 1.55 | 0.83 |
| 6 | 0.37 | 2.52 | 3.46 | 0.42 | 0.60 |
| Average | 0.09 | 2.45 | 4.49 | 2.25 | 0.48 |
| Std. Dev. | 0.276 | 0.567 | 1.227 | 1.202 | 0.250 |
| $T_c$[e] | 0.799 | 10.584 | 8.93 | 4.585 | 4.293 |
| Stat. Diff.[f] | No | Yes | Yes | Yes | Yes |

[a]The percentage difference is calculated from the formulas:
Treated Site Percentage Difference = 100*[((Treated Site$_t$ - Treated Site$_{Before Cleansing}$)/Treated Site$_{Before Cleansing}$)]
Untreated Site Percentage Difference 100*[((Untreated Site$_t$ - Untreated Site$_{Before Cleansing}$)/Untreated Site$_{Before Cleansing}$)]
[b]The matched pair in each case is calculated from the formula:
Value = Value for Treated Site$_t$ - Valued for Untreated Site$_t$
[c]Reading taken after cleansing both sites with a skin cleanser as described in test methodology.
[d]NR - No reading taken because of subject unavailability
[e]Calculated statistical Student t value.
[f]Statistical difference at the 95% confidence interval using a 2-tailed test.

TABLE 11

Statistical Evaluation of Sebutape Percentage Difference Readings[a] from Baseline (Before Cleansing) of Skin Treated with Test Formula Versus Skin Not Treated With the Test Formula Using a Matched Pairs Technique[b]
Formula D (0% Pyridoxine Hydrochloride (Vitamin $B_6$))

| Subject No. | Initial Reading[c] | 1 Hour Reading | 2 Hour Reading | 4 Hour Reading | 6 Hour Reading |
|---|---|---|---|---|---|
| 1 | 0.07 | 1.30 | 3.89 | 2.14 | −0.07 |
| 2 | −0.26 | 1.19 | 2.21 | 0.13 | −0.13 |
| 3 | 0.10 | 1.00 | 1.67 | 0.01 | −0.61 |
| 4 | 0.41 | 1.22 | 1.93 | 1.15 | 0.30 |
| 5 | −0.10 | 1.65 | 2.85 | 1.62 | −0.13 |
| Average | 0.05 | 1.27 | 2.51 | 1.01 | −0.13 |
| Std. Dev. | 0.249 | 0.240 | 0.885 | 0.926 | 0.326 |
| $T_c$[c] | 0.449 | 11.833 | 6.342 | 2.439 | 0.892 |
| Stat. Diff.[d] | No | Yes | Yes | No | No |

[a]The percentage difference is calculated from the formulas:
Treated Site Percentage Difference 100*[((Treated Site$_t$ - Treated Site$_{Before Cleansing}$)/Treated Site$_{Before Cleansing}$)]
Untreated Site Percentage Difference 100*[((Untreated Site$_t$ - Untreated Site$_{Before Cleansing}$)/Untreated Site$_{Before Cleansing}$)]
[b]The matched pair in each case is calculated from the formula:
Value = Value for Treated Site$_t$ - Valued for Untreated Site$_t$
[c]Reading taken after cleansing both sites with a skin cleanser as described in test methodology.
[d]Calculated statistical Student t value.
[e]Statistical difference at the 95% confidence interval using a 2-tailed test.

The percentage difference in the amounts of skin oils produced between the treated and untreated skin sites is as follows:

When compared to the untreated skin prior to being cleansed as expressed in terms of the amount of time following the application of the test product:

| | Formula D (0% Vitamin $B_6$) | Formula C (0.025% Vitamin $B_6$) |
|---|---|---|
| 1 Hour after application | 1.27% | 2.45% |
| 2 Hours after application | 2.51% | 4.49% |
| 4 Hours after application | 1.01% | 2.25% |
| 6 Hours after application | −0.13% | 0.48% |

Figure 3:
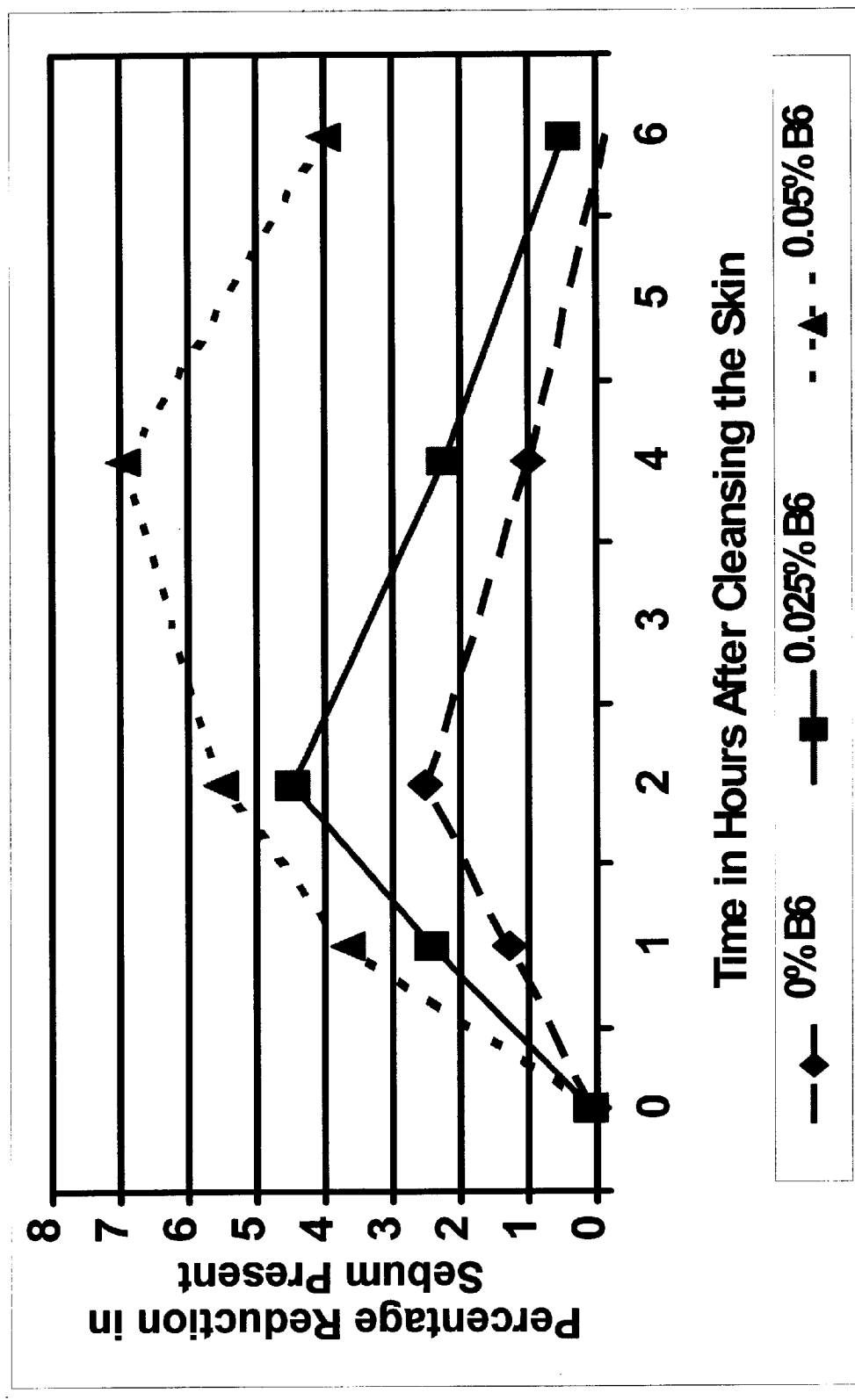
FIG. 3 is a graph demonstrating the effect of vitamin $B_6$ on the level of sebum present on the skin. The results are expressed as the difference in percent between treated and untreated skin prior to cleansing. The results are expressed as the percentage reduction in sebum present at each time point.

These results are graphically shown in FIG. 3.

When compared to freshly cleansed skin (using the test product) as expressed in terms of the amount of time following application of the test product:

| | Formula D (0% Vitamin $B_6$) | Formula C (0.025% Vitamin $B_6$) |
|---|---|---|
| 1 Hour after application | 1.09% | 2.02% |
| 2 Hours after application | 2.18% | 3.76% |
| 4 Hours after application | 0.85% | 1.83% |
| 6 Hours after application | −0.15% | 0.39% |

Figure 4:
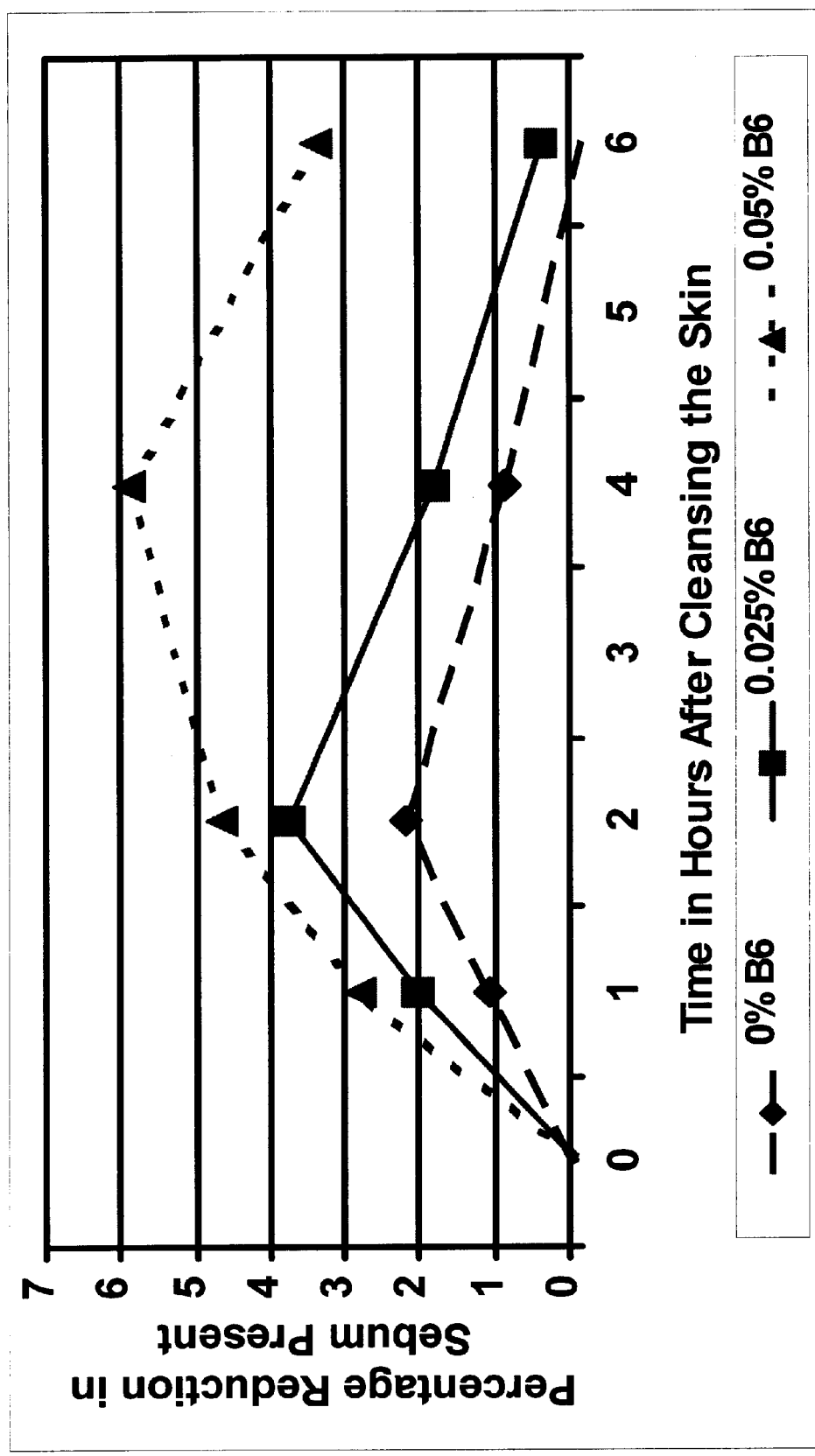
FIG. 4 is a second graph demonstrating the effect of vitamin $B_6$ on the level of sebum present on freshly cleansed skin. The results are expressed as the difference in percent between treated and untreated skin after cleansing. The results are expressed as the percentage reduction in sebum present at each time point.

These results are graphically shown in FIG. 4.

These results clearly demonstrate that the treatment of the skin with the test formulations containing either 0% or 0.025% Pyridoxine Hydrochloride (Vitamin $B_6$) are effective at reducing the appearance of surface skin oils. However, neither of these formulations is as effective as the combination containing 0.05% Pyridoxine Hydrochloride (see Table 1). The test results reveal that the effectiveness of Formula C lasts for up to 6 hours following a single application of the product.

A careful evaluation of the results as shown in FIGS. 3 and 4 clearly indicate that the 0.050% Pyridoxine Hydrochloride (Vitamin $B_6$) formula exhibits synergy that is unexpected. This is evidenced by the fact that the graph for the formulation containing 0.05% Vitamin $B_6$ is more effective at 4 and 6 hours than the other formulas evaluated. Furthermore, given the data listed above, the effectiveness expected from the 0.05% Vitamin $B_6$ formulation is more the difference in the 0 and 0.025% Vitamin $B_6$ containing formulations. The following data demonstrates that difference.

| | Percentage Reduction in Sebum | | |
|---|---|---|---|
| Evaluation Time | Theoretical[a] | Actual | Difference |
| For Results Obtained Before Cleansing the Skin | | | |
| 1 hour | 3.63% | 3.68% | 0.05% |
| 2 hours | 6.47% | 5.53% | −0.94% |
| 3 hours | 3.49% | 6.95% | 3.46% |
| 4 hours | 1.09% | 4.01% | 2.92% |
| For Results Obtained from Freshly Cleansed Skin | | | |
| 1 hour | 2.95% | 2.79% | −0.16% |
| 2 hours | 5.34% | 4.67% | −0.67% |
| 3 hours | 2.81% | 5.87% | 3.06% |
| 4 hours | 0.93% | 3.39% | 2.46% |

[a]Calculated from the difference between the 0% and 0.025% Vitamin $B_6$ formulations, corrected for the additional 0.025% Vitamin $B_6$ and then added to the baseline value assumed to be the 0% Vitamin $B_6$ value.

Example 6

Effect of Zinc Gluconate (Solublized Zinc)

The effect of the presence of the Zinc Gluconate on the effectiveness of the formulation was evaluated. Specifically, two formulations were evaluated to determine the effect of zinc gluconate, in formulations E and F of Table 5. Formula E contains half the amount of Zinc Gluconate contained in the original formula (see Table 1) whereas Formula F does not contain any Zinc Gluconate.

The spectrophotometrically measured amounts of sebum present on untreated, uncleansed skin as measured with Sebutape on the forehead of the test subjects using these two formulations were compared. These results clearly shows that the average values for the treated and untreated sites prior to cleansing were not statistically different at the 95% confidence interval. A matched-pairs evaluation of these same results was also conducted. Again, these results were not statistically different as determined by this statistical evaluation method.

The effects of the amount of Zinc Gluconate on the efficacy of this product was determined for spectrophotometrically measured amounts of sebum on the surface of the skin. The data clearly shows that the side of the forehead treated with these test formulations exhibit a lower amount of surface sebum at 1 hour (an average whiteness value of 84.79±0.418 for the treated group as compared to an average whiteness value of 82.92±0.985 for the untreated group) and 2 hours (an average whiteness value of 83.20±0.854 for the treated group as compared to an average whiteness value of 80.46±1.660 for the untreated group) after treatment for Formula E. This data clearly shows that the side of the forehead treated with test Formula F exhibits a lower amount of surface sebum at 1 hour (an average whiteness value of 83.04±0.316 for the treated group as compared to an average whiteness value of 81.96±0.346 for the untreated group), 2 hours (an average whiteness value of 80.63±0.291 for the treated group as compared to an average whiteness value of 78.48±0.468 for the untreated group) and 4 hours (an average whiteness value of 75.72±0.756 for the treated group as compared to an average whiteness value of 74.69±0.290 for the untreated group) after treatment. These differences are statistically significant at the 95% confidence level at each of these evaluation points, as evaluated by the 2-tailed test. However, the difference between the treated and untreated sites is not statistically significantly different at 6 hours for either sample or at 4 hours for the 0.25% Zinc Gluconate formula (Formula E). They are also not statistically different immediately following the cleansing process.

A somewhat different picture is obtained when the results for these formulations are evaluated by a matched-pairs statistical technique as shown below in Tables 12 and 13.

TABLE 12

Statistical Evaluation of Sebutape Readings of Skin Treated with Test Formula Versus Cleansed Skin Not Treated With the Test Formula by a Matched Pairs Technique[a]
Formula E (0.25% Zinc Gluconate)

| Subject No. | Initial Reading[b] | After Cleansing Reading | 1 Hour Reading | 2 Hour Reading | 4 Hour Reading | 6 Hour Reading |
|---|---|---|---|---|---|---|
| 1 | −0.01 | 0.08 | 2.16 | 3.16 | 2.15 | 0.32 |
| 2 | 0.27 | −0.01 | 0.87 | 1.40 | 1.67 | 0.47 |
| 3 | −0.08 | 0.33 | 2.22 | 3.76 | 1.73 | 0.97 |
| 4 | 0.36 | −0.30 | 1.65 | 2.36 | 0.79 | 0.57 |
| 5 | −0.10 | −0.15 | 2.46 | 3.00 | 2.13 | 0.40 |
| Average | 0.09 | −0.01 | 1.87 | 2.74 | 1.69 | 0.55 |
| Std. Dev. | 0.212 | 0.238 | 0.633 | 0.898 | 0.552 | 0.254 |
| $t_c$[c] | 0.949 | 0.094 | 6.606 | 6.823 | 6.846 | 4.842 |
| Stat. Diff.[d] | No | No | Yes | Yes | Yes | Yes |

[a]The matched pair in each case is calculated from the formula:
Value = Value for Treated Site$_t$ - Valued for Untreated Site$_t$
[b]Reading taken after cleansing both sites with a skin cleanser as described in test methodology.
[c]Calculated statistical Student t value.
[d]Statistical difference at the 95% confidence interval using a 2-tailed test.

TABLE 13

Statistical Evaluation of Sebutape Readings of Skin Treated with Test Formula Versus Cleansed Skin Not Treated With the Test Formula by a Matched Pairs Technique[a]
Formula F (0% Zinc Gluconate)

| Subject No. | Initial Reading[b] | After Cleansing Reading | 1 Hour Reading | 2 Hour Reading | 4 Hour Reading | 6 Hour Reading |
|---|---|---|---|---|---|---|
| 1 | 0.08 | −0.10 | 1.07 | 1.71 | 1.92 | 0.81 |
| 2 | −0.28 | −0.06 | 0.95 | 2.17 | 1.25 | 0.19 |
| 3 | 0.08 | −0.35 | 1.14 | 2.75 | 1.08 | 0.18 |
| 4 | −0.06 | 0.35 | 0.99 | 2.01 | 0.64 | NR[c] |
| 5 | 0.05 | 0.26 | 1.22 | 2.13 | 0.28 | −0.13 |
| Average | −0.03 | 0.02 | 1.07 | 2.15 | 1.03 | 0.26 |
| Std. Dev. | 0.153 | 0.258 | 0.110 | 0.379 | 0.624 | 0.394 |
| $t_c$[c] | 0.438 | 0.157 | 21.751 | 12.685 | 3.301 | 1.476 |
| Stat. Diff.[e] | No | No | Yes | Yes | Yes | No |

[a]The matched pair in each case is calculated from the formula:
Value = Value for Treated Site$_t$ - Valued for Untreated Site$_t$
[b]Reading taken after cleansing both sites with a skin cleanser as described in test methodology.
[c]NR - No reading taken because of subject unavailability
[d]Calculated statistical Student t value.
[e]Statistical difference at the 95% confidence interval using a 2-tailed test.

Using this powerful statistical technique, the results for both formulas become statistically significant at 1, 2, and 4 hours. The results for Formula E (0.250% Zinc Gluconate) also becomes significant at 6 hours. The remaining results are not statistically significant. Given the power to discern a smaller level of differences using matched pairs statistical methods, the differences found using this technique are not only real, but also important.

The spectrophotometrically measured amounts of sebum were then calculated as the percentage difference between the freshly cleansed skin and other evaluation points. In this method of evaluation, the differences between the treated and untreated sites for either Formulas E and F were not statistically different for the initial evaluation (Day 1 results) or at the 6 hour evaluation. However, after the test product has been applied to the treatment sites, the results were statistically different at the 95% confidence level (2-tailed test) at 1 and 2 hours for both formulas as well as at 4 hours for Formula F (0% Zinc Gluconate).

A somewhat different picture was obtained when the results for these formulations are evaluated by a matched-pairs statistical technique (see Tables 14 and 15, below).

TABLE 14

Statistical Evaluation of Sebutape Percentage Difference Readings[a] from Baseline (After Cleansing) of Skin Treated with Test Formula Versus Cleansed Skin Not Treated With the Test Formula Using a Matched Pairs Technique[b]
Formula E (0.25% Zinc Gluconate)

| Subject No. | Initial Reading[c] | 1 Hour Reading | 2 Hour Reading | 4 Hour Reading | 6 Hour Reading |
|---|---|---|---|---|---|
| 1 | −0.09 | 2.44 | 3.61 | 2.43 | 0.30 |
| 2 | 0.32 | 1.02 | 1.64 | 1.95 | 0.56 |
| 3 | −0.42 | 2.22 | 4.03 | 1.68 | 0.80 |
| 4 | 0.72 | 2.25 | 3.06 | 1.23 | −1.08 |
| 5 | 0.04 | 3.03 | 3.66 | 2.64 | 0.63 |
| Average | 0.11 | 2.19 | 3.20 | 1.99 | 0.24 |
| Std. Dev. | 0.433 | 0.731 | 0.939 | 0.569 | 0.761 |
| $T_c{}^c$ | 0.568 | 6.700 | 7.620 | 7.820 | 0.705 |
| Stat. Diff.[e] | No | Yes | Yes | Yes | No |

[a]The percentage difference is calculated from the formulas:
Treated Site Percentage Difference 100*[((Treated Site$_{Before\ Cleansing}$ - Treated Site$_t$)/Treated Site$_{After\ Cleansing}$)]
Untreated Site Percentage Difference = 100*[((Untreated Site$_{After\ Cleansing}$ - Untreated Site$_t$)/Untreated Site$_{After\ Cleansing}$)]
[b]The matched pair in each case is calculated from the formula:
Value = Value for Treated Site$_t$ - Valued for Untreated Site$_t$
[c]Reading taken before cleansing both sites with a skin cleanser as described in test methodology.
[d]Calculated statistical Student t value.
[e]Statistical difference at the 95% confidence interval using a 2-tailed test.

TABLE 15

Statistical Evaluation of Sebutape Percentage Difference Readings[a] from Baseline (After Cleansing) of Skin Treated with Test Formula Versus Cleansed Skin Not Treated With the Test Formula Using a Matched Pairs Technique[b]
Formula F (0% Zinc Gluconate)

| Subject No. | Initial Reading[c] | 1 Hour Reading | 2 Hour Reading | 4 Hour Reading | 6 Hour Reading |
|---|---|---|---|---|---|
| 1 | 0.19 | 1.38 | 2.13 | 2.37 | 1.06 |
| 2 | −0.27 | 1.19 | 2.63 | 1.54 | 0.28 |
| 3 | 0.44 | 1.75 | 3.64 | 1.64 | 0.57 |
| 4 | −0.43 | 0.77 | 1.99 | 0.39 | NR[d] |
| 5 | −0.21 | 1.14 | 2.23 | 0.06 | −0.42 |
| Average | −0.05 | 1.25 | 2.52 | 1.20 | 0.37 |
| Std. Dev. | 0.360 | 0.358 | 0.667 | 0.954 | 0.618 |
| $T_c{}^c$ | 0.311 | 7.807 | 8.448 | 2.516 | 1.339 |
| Stat. Diff.[f] | No | Yes | Yes | No | No |

[a]The percentage difference is calculated from the formulas:
Treated Site Percentage Difference 100*[((Treated Site$_{After\ Cleansing}$ - Treated Site$_t$)/Treated Site$_{After\ Cleansing}$)]
Untreated Site Percentage Difference = 100*[((Untreated Site$_{After\ Cleansing}$ - Untreated Site$_t$)/Untreated Site$_{After\ Cleansing}$)]
[b]The matched pair in each case is calculated from the formula:
Value = Value for Treated Site$_t$ - Valued for Untreated Site$_t$
[c]Reading taken before cleansing both sites with a skin cleanser as described in test methodology.
[d]NR - No reading taken because of subject unavailability
[e]Calculated statistical Student t value.
[f]Statistical difference at the 95% confidence interval using a 2-tailed test.

Using this powerful statistical technique, the results for both formulas become statistically significant at 1 and 2 hours. The results for Formula E (0.250% Zinc Gluconate) also becomes significant at 4 hours. The remaining results are not statistically significant. Given the power to discern a smaller level of differences using matched pairs statistical methods, the differences found using this technique are both real and important.

The percentage difference results between the initial (Day 1) results and the data at the other evaluation points for Formulas E and F were also statistically evaluated. The statistical evaluation of this data revealed the same outcome as found previously for the percentage difference from the freshly cleansed and treated skin. The percentage difference in the freshly cleansed of the treatment site and the freshly cleansed of the control site are not statistically different. The results at the 6 hour evaluation point were also not statistically significant. Additionally, the results for Formula E at the 4 hour time-point were not statistically significant. However, the percentage difference between the treated and untreated sites is statistically different at 1 and 2 hours following the application of either of these two test formulas (Formulas E and F) as well as at 4 hours for Formula E (0% Zinc Gluconate).

A significantly different picture is found when the data is evaluated using a matched-pairs statistical. Using this statistical technique, Formula E (0.25% Zinc Gluconate) exhibited statistically significant differences at 1, 2, 4 and 6 hours whereas Formula F (0% Zinc Gluconate) showed statistically significant differences at the 1, 2, and 4 hours evaluation points but not at the 6 hour evaluation.

The percentage difference in the amounts of skin oils produced between the treated and untreated skin sites is as follows:

When compared to the untreated skin prior to being cleansed as expressed in terms of the amount of time following the application of the test product:

|  | Formula E<br>(0% Zinc) | Formula F<br>(0.250% Zinc) |
|---|---|---|
| 1 Hour after application | 1.52% | 2.36% |
| 2 Hours after application | 3.01% | 3.52% |
| 4 Hours after application | 1.47% | 2.12% |
| 6 Hours after application | 0.39% | 0.75% |

Figure 5:
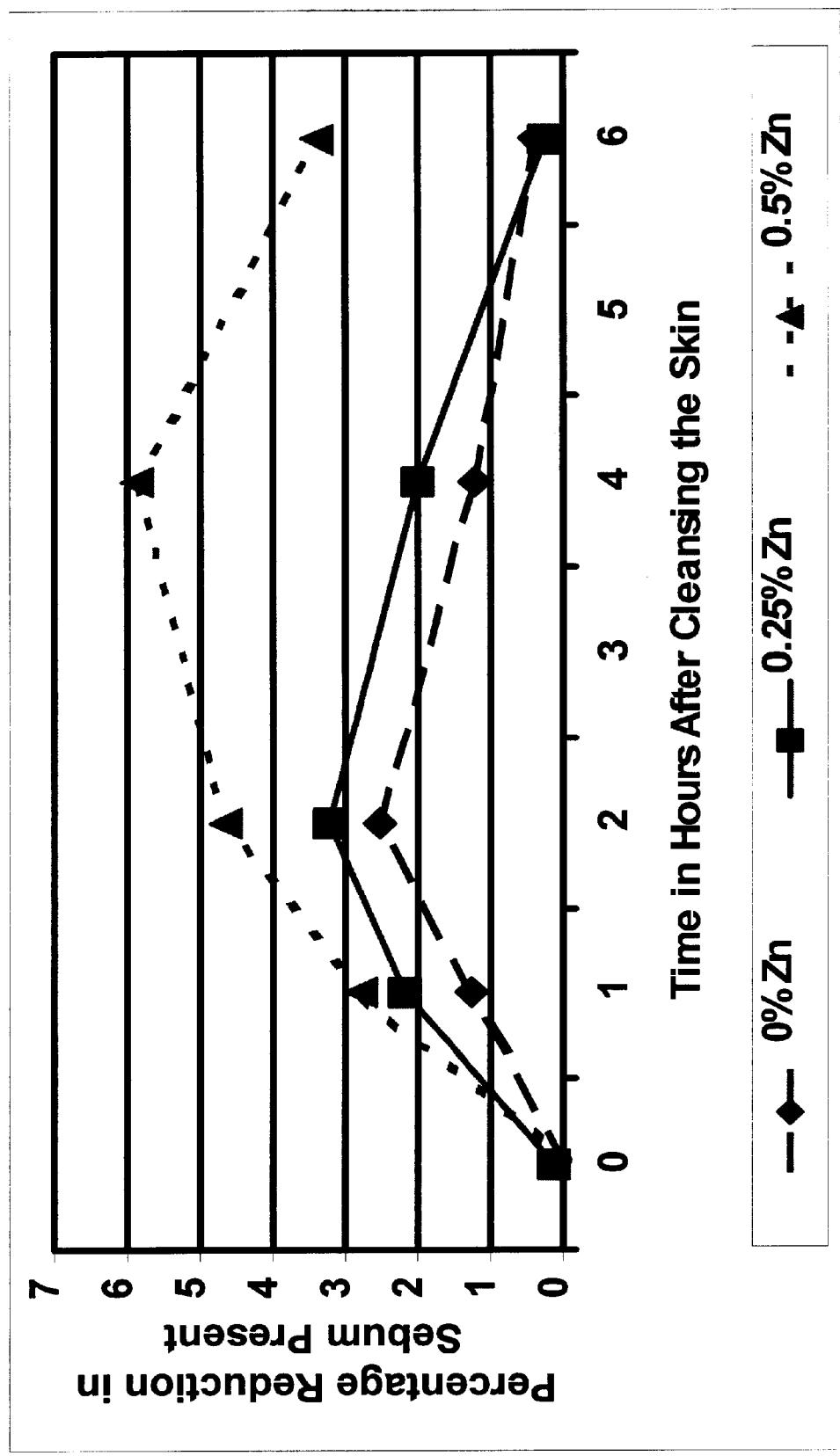
FIG. 5 is a graph demonstrating the effect of Zinc Gluconate on the level of sebum present on the skin. The results are expressed as the difference in percent between treated and untreated skin prior to cleansing. The results are expressed as the percentage reduction in sebum present at each time point.

These results are graphically shown in FIG. 5.

When compared to freshly cleansed skin (using the test product) as expressed in terms of the amount of time following application of the test product:

|  | Formula E<br>(0% Zinc) | Formula F<br>(0.250% Zinc) |
|---|---|---|
| 1 Hour after application | 1.25% | 2.19% |
| 2 Hours after application | 2.52% | 3.20% |
| 4 Hours after application | 1.20% | 1.99% |
| 6 Hours after application | 0.37% | 0.24% |

Figure 6:
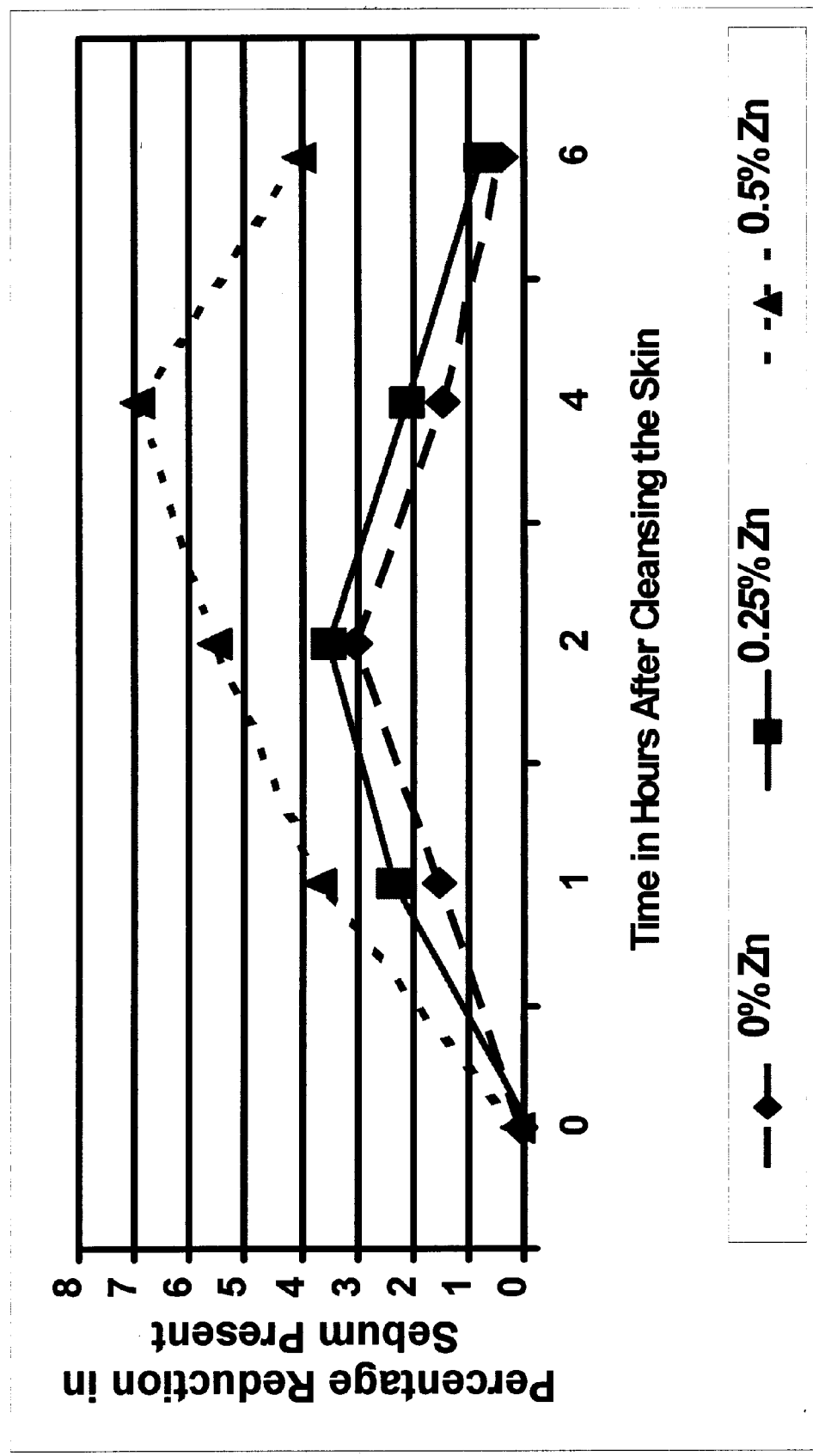
FIG. 6 is a second graph demonstrating the effect of Zinc Gluconate on the level of sebum present on freshly cleansed skin. The results are expressed as the difference in percent between treated and untreated skin after cleansing. The results are expressed as the percentage reduction in sebum present at each time point.

These results are graphically shown in FIG. 6.

These results clearly demonstrate that the treatment of the skin with the test formulations containing either 0% or 0.250% Zinc Gluconate was effective at reducing the appearance of surface skin oils. However, neither of these formulations were as effective as the combination containing 0.500% Zinc Gluconate (see Table 1). The test results revealed that the effectiveness of Formulas E and F lasted for up to 6 hours following a single application of the product.

A careful evaluation of the results as shown in FIGS. 5 and 6 clearly indicate that the 0.05% Zinc Gluconate formula exhibits synergy that is unexpected. This is evidenced by the fact that the graph for the formulation containing 0.500% Zinc Gluconate is more effective at 4 and 6 hours than the other formulas evaluated. Furthermore, given the data listed above, the effectiveness expected from the 0.500% Zinc Gluconate formulation is more the difference in the 0 and 0.250% Zinc Gluconate containing formulations. The data shown below demonstrates that difference.

| Evaluation Time | Percentage Reduction in Sebum | | |
|---|---|---|---|
|  | Theoretical[a] | Actual | Difference |
| For Results Obtained Before Cleansing the Skin: | | | |
| 1 hour | 3.20% | 3.68% | 0.48% |
| 2 hours | 4.03% | 5.53% | 1.50% |
| 3 hours | 2.77% | 6.95% | 4.18% |
| 4 hours | 1.11% | 4.01% | 2.90% |
| For Results Obtained from Freshly Cleansed Skin: | | | |
| 1 hour | 3.13% | 2.79% | −0.34% |
| 2 hours | 3.88% | 4.67% | 0.79% |
| 3 hours | 2.78% | 5.87% | 3.09% |
| 4 hours | 0.37% | 3.39% | 3.02% |

[a]Calculated from the difference between the 0% and 0.250% Zinc Gluconate formulations, corrected for the additional 0.250% Zinc Gluconate and then added to the baseline value assumed to be the 0% Zinc Gluconate value.

Example 7

Effect of Simultaneously Reduced Levels of SD Alcohol 40-B, Pyridoxine Hydrochloride, and Zinc Gluconate As the effect of the presence of the individual components (SD Alcohol 40-B, Pyridoxine Hydrochloride, and Zinc Gluconate) was evaluated on the effectiveness of the formulation, the effect of the combination of the ingredients at half their original concentrations (as shown in Formula G in Table 5) was also evaluated.

A comparison was conducted on Day 1 between the spectrophotometrically measured amounts of sebum present on untreated, uncleansed skin as measured with Sebutape on the forehead of the test subjects using these 2 formulations. These results clearly showed that the average values for the treated and untreated sites prior to cleansing were not statistically different at the 95% confidence interval. The matched-pairs evaluation of these same results demonstrated that the results are not statistically different.

The effects of the amount of the reduced concentration of these three ingredients on the efficacy of this product was determined for spectrophotometrically measured amounts of sebum on the surface to the skin, both for the skin treated with the test formulation and for the untreated skin. This data clearly showed that the side of the forehead treated with these test formulations exhibit a lower amount of surface sebum at 1 hour (an average whiteness value of 83.63±0.561 for the treated group as compared to an average whiteness value of 82.45±0.958 for the untreated group), 2 hours (an average whiteness value of 81.21±0.924 for the treated group as compared to an average whiteness value of 79.21±1.845 for the untreated group), and 4 hours (an average whiteness value of 77.22±1.382 for the treated group as compared to an average whiteness value of 74.44±1.681 for the untreated group) after treatment for both Formula G. These differences are statistically significant at the 95% confidence level (2-tailed test) at each of these evaluation points. However, this difference between the treated and untreated sites was not statistically significantly different at 6 hours for either sample. They were also not statistically different immediately following the cleansing process or when measured the previous day.

A somewhat different picture was obtained when the results for these formulations were evaluated by a matched-pairs statistical technique as shown in Table 16.

TABLE 16

Statistical Evaluation of Sebutape Readings of Skin Treated with Test Formula Versus Cleansed Skin Not Treated With the Test Formula by a Matched Pairs Technique[a]
Formula G (0.025% Pyridoxine Hydrochloride Vitamin $B_6$), 0.25% Zinc Gluconate, and 5% SD Alcohol 40-B)

| Subject No. | Initial Reading[b] | After Cleansing Reading | 1 Hour Reading | 2 Hour Reading | 4 Hour Reading | 6 Hour Reading |
|---|---|---|---|---|---|---|
| 1 | 0.57 | 0.00 | 1.98 | 4.64 | 3.25 | 0.71 |
| 2 | 0.08 | 0.05 | 0.68 | 2.13 | 2.47 | 1.60 |
| 3 | −0.06 | 0.01 | 0.61 | 1.80 | 1.97 | 0.68 |
| 4 | −0.04 | 0.02 | 1.31 | 2.31 | 2.13 | 0.81 |
| 5 | 0.40 | −0.06 | 1.01 | 2.34 | 2.42 | 0.61 |
| 6 | 0.17 | 0.02 | 1.47 | 2.42 | 4.46 | −0.12 |
| Average | 0.19 | 0.01 | 1.18 | 2.61 | 2.78 | 0.72 |
| Std. Dev. | 0.252 | 0.037 | 0.519 | 1.020 | 0.932 | 0.548 |

TABLE 16-continued

Statistical Evaluation of Sebutape Readings of Skin Treated with
Test Formula Versus Cleansed Skin Not Treated With the Test
Formula by a Matched Pairs Technique[a]
Formula G (0.025% Pyridoxine Hydrochloride Vitamin $B_6$),
0.25% Zinc Gluconate, and 5% SD Alcohol 40-B)

| Subject No. | Initial Reading[b] | After Cleansing Reading | 1 Hour Reading | 2 Hour Reading | 4 Hour Reading | 6 Hour Reading |
|---|---|---|---|---|---|---|
| $t_c^c$ | 1.847 | 0.662 | 5.569 | 6.268 | 7.306 | 3.218 |
| Stat. Diff.[d] | No | No | Yes | Yes | Yes | Yes |

[a]The matched pair in each case is calculated from the formula: Value = Value for Treated $Site_t$ - Valued for Untreated $Site_t$
[b]Reading taken after cleansing both sites with a skin cleanser as described in test methodology.
[c]Calculated statistical Student t value.
[d]Statistical difference at the 95% confidence interval using a 2-tailed test.

Using this powerful statistical technique, the results for both formulas became statistically significant at 1, 2, 4, and 6 hours. The remaining results are not statistically significant. Given the power to discern a smaller level of differences using matched pairs statistical methods, the differences found using this technique were not only real, but also important.

The spectrophotometrically measured amounts of sebum were then calculated as the percentage difference between the freshly cleansed skin and other evaluation points. In this method of evaluation, the differences between the treated and untreated sites for Formula G were not statistically different for the initial evaluation (Day 1 results) or at the 6 hour evaluation. Again a somewhat different picture is obtained when the results for these formulations were evaluated by a matched-pairs statistical technique as shown in Table 17.

TABLE 17

Statistical Evaluation of Sebutape Percentage Difference Readings[a]
from Baseline (After Cleansing) of Skin
Treated with Test Formula Versus Cleansed Skin Not Treated With
the Test Formula Using a Matched Pairs Technique[b]
Formula G (0.025% Pyridoxine Hydrochloride (Vitamin $B_6$),
0.25% Zinc Gluconate, and 5% SD Alcohol 40-B)

| Subject No. | Initial Reading[c] | 1 Hour Reading | 2 Hour Reading | 4 Hour Reading | 6 Hour Reading |
|---|---|---|---|---|---|
| 1 | 0.67 | 2.33 | 5.46 | 3.82 | 0.83 |
| 2 | 0.04 | 0.74 | 2.46 | 2.86 | 1.84 |
| 3 | -0.08 | 0.71 | 2.11 | 2.31 | 0.79 |
| 4 | -0.07 | 1.52 | 2.69 | 2.48 | 0.93 |
| 5 | 0.53 | 1.26 | 2.82 | 2.91 | 0.78 |
| 6 | 0.18 | 1.71 | 2.83 | 5.23 | -0.16 |
| Average | 0.21 | 1.38 | 3.06 | 3.27 | 0.84 |
| Std. Dev. | 0.318 | 0.616 | 1.204 | 1.093 | 0.635 |
| $T_c^d$ | 1.618 | 5.487 | 6.225 | 7.328 | 3.240 |
| Stat. Diff.[e] | No | Yes | Yes | Yes | Yes |

[a]The percentage difference is calculated from the formulas:
Treated Site Percentage Difference = 100*[((Treated $Site_{After\ Cleansing}$ - Treated $Site_t$)/Treated $Site_{After\ cleansing}$)]
Untreated Site Percentage Difference = 100*[((Untreated $Site_{After\ Cleansing}$ - Untreated $Site_t$)/Untreated $Site_{After\ Cleansing}$)]
[b]The matched pair in each case is calculated from the formula: Value = Value for Treated $Site_t$ - Valued for Untreated $Site_t$
[c]Reading taken before cleansing both sites with a skin cleanser as described in test methodology.
[d]Calculated statistical Student t value.
[e]Statistical difference at the 95% confidence interval using a 2-tailed test.

Using this powerful statistical technique, the results for this formula are only statistically significant at 1, 2, 4, and 6 hours.

The percentage difference results between the initial (Day 1) results and the data at the other evaluation points for Formula G of Table 5 were statistically evaluated. The statistical evaluation of the percentage difference reveals the same outcome as found previously for the percentage difference from the freshly cleansed and treated skin. The percentage difference in the freshly cleansed of the treatment site and the freshly cleansed of the control site are not statistically different. The results at the 6 hour evaluation point also were not statistically significant.

The percentage difference in the amounts of skin oils produced between the treated and untreated skin sites is as follows:

When compared to the untreated skin prior to being cleansed as expressed in terms of the amount of time following the application of the test product:

|  | Formula G (50% of Each) | Intact Formula[a] (106% of Each) |
|---|---|---|
| 1 Hour after application | 1.33% | 3.68% |
| 2 Hours after application | 3.35% | 5.53% |
| 4 Hours after application | 3.61% | 6.95% |
| 6 Hours after application | 0.72% | 4.01% |

Figure 7:
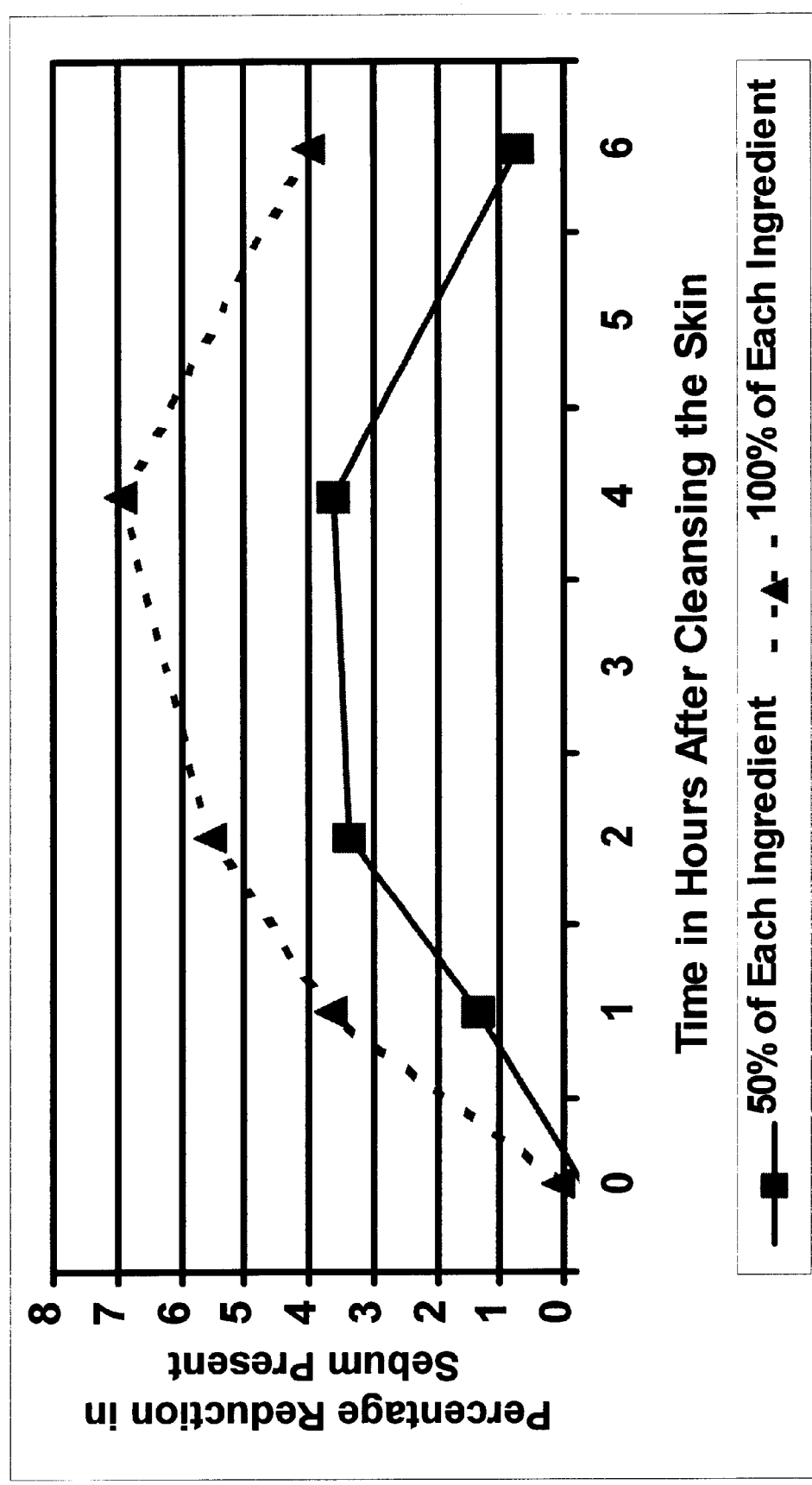
FIG. 7 is a graph of the combined effect of SD Alcohol 40-B, Pyridoxine Hydrochloride (Vitamin $B_6$), and Zinc Gluconate on the sebum present on the skin expressed calculated as the difference in percent between treated and untreated skin sites prior to cleansing.

These results are graphically shown in FIG. 7.

When compared to freshly cleansed skin (using the test product) as expressed in terms of the amount of time following application of the test product:

|  | Formula G (50% of Each) | Intact Formula[a] (100% of Each) |
|---|---|---|
| 1 Hour after application | 1.38% | 2.79% |
| 2 Hours after application | 3.06% | 4.67% |
| 4 Hours after application | 3.27% | 5.87% |
| 6 Hours after application | 0.84% | 3.39% |

[a]Results after application of the formula shown in Table 1.

Figure 8:
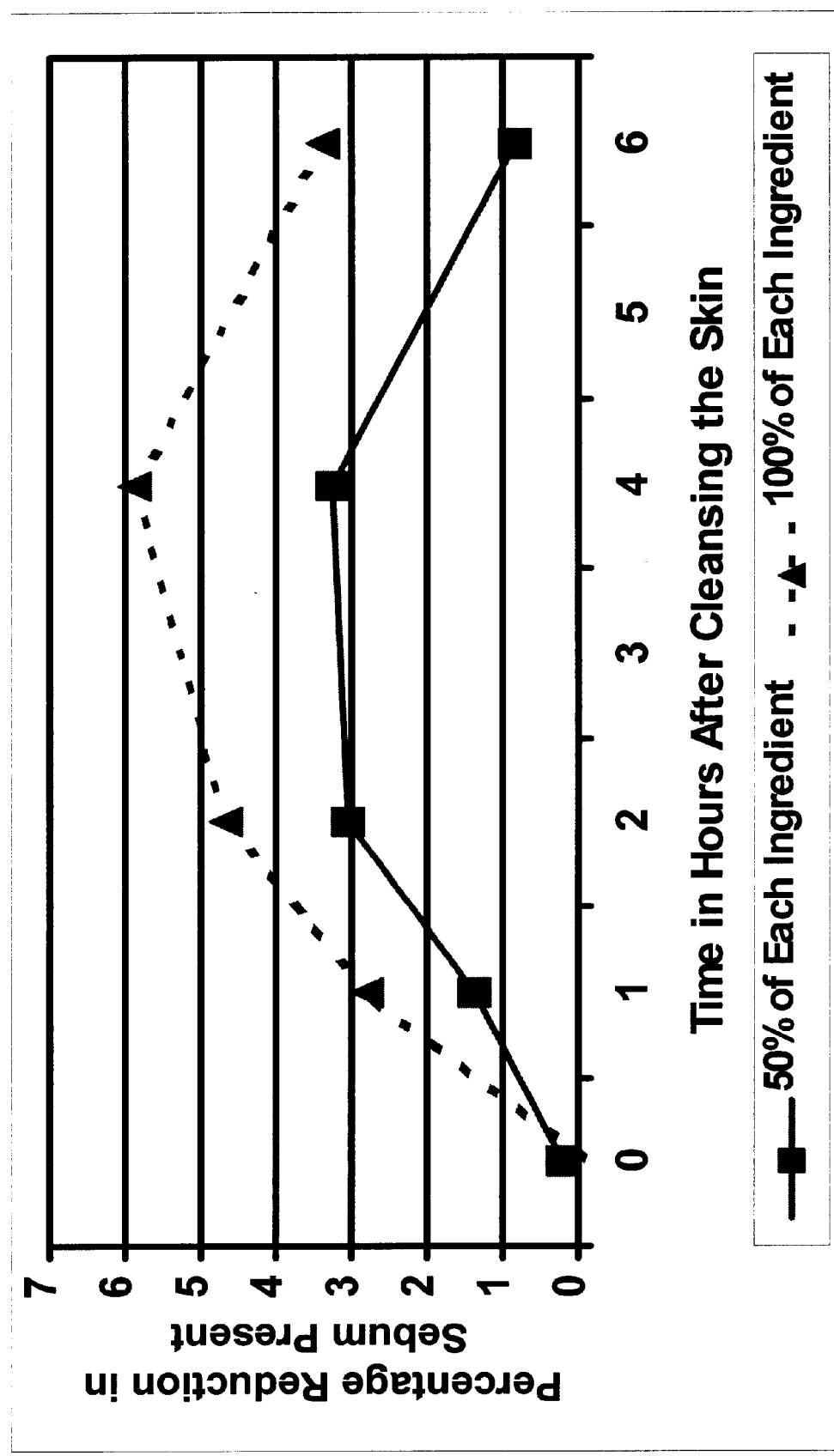
FIG. 8 is a second graph demonstrating the combined effect of SD Alcohol 40-B, Pyridoxine Hydrochloride (Vitamin $B_6$), and Zinc Gluconate on the sebum present on the skin expressed calculated as the difference in percent between treated and untreated skin sites after cleansing.

These results are graphically shown in FIG. 8.

These results clearly demonstrated that the treatment of the skin with the test formulation containing half of each of the active ingredients was effective in reducing the appearance of surface skin oils. Although this formulation was not as effective as the intact formulation shown in Table 1, the test results reveal that the effectiveness of Formula G did last for up to 6 hours following a single application of the product.

Example 8

The Reduction in Surface Sebum Provides a Perceptible Difference in Human Subjects Not only was there a significant reduction in surface sebum, but the formulations containing a vitamin B6 derivative, a zinc salt, and an alcohol can change skin-feel. The product listed in Table 1 was used by 30 otherwise healthy subjects with acne for a period of 4 weeks. At the end of that period, they were asked a variety of questions via a questionnaire. Among the questions asked was one pertaining to their perception that this formulation reduced the appearance of skin oils. Those subjects clearly indicated that this product reduced the perception of skin oiliness. Therefore, the amount of reduction in surface sebum provided by a formulation of the invention has been shown to have a consumer perceptible benefit.

Thus, the formulations of the invention deliver a definite reduction in the oiliness when applied to the skin of human subjects. The efficacy of this formulation lasts for up to 6 hours following a single application. That effectiveness is a result of a combination of SD Alcohol 40-B, Pyridoxine Hydrochloride (Vitamin $B_6$), and Zinc Gluconate incorporated into the formulation. This same efficacy could be obtained from a combination of any short chain alcohol (such as methyl alcohol, propyl alcohol, isopropyl alcohol, butyl alcohol, isobutyl alcohol, t-butyl alcohol, or any of the various pentyl, hexyl or heptyl alcohols), any salt or derivative of Vitamin $B_6$ (such as Pyridoxine Hydronitrate, Hydroacetate, or amide, etc.), and any soluble zinc salt (such as zinc nitrate, zinc chloride, zinc acetate, etc.).

Each of these ingredients have been shown to be effect in a range of concentrations. The range of concentrations necessary for the purposes of this disclosure are as follows:

| | |
|---|---|
| Short Chain Alcohol | about 0.01 to 40% |
| Salt of Vitamin $B_6$ | about 0.00001 to 5% |
| Soluble Zinc Salt | about 0.0001 to 10% |

In one embodiment, the range of concentrations of these ingredients is as follows:

| | |
|---|---|
| Short Chain Alcohol | about 1 to 20% |
| Salt of Vitamin $B_6$ | about 0.001 to 1% |
| Soluble Zinc Salt | about 0.01 to 4% |

In anther embodiment, the range of concentrations of these ingredients is as follows:

| | |
|---|---|
| Short Chain Alcohol | about 5 to 15% |
| Salt of Vitamin $B_6$ | about 0.01 to 0.5% |
| Soluble Zinc Salt | about 0.1 to 2% |

Example 9

Other Formulations

Alternative formulations for composition of the invention are shown in Table 18 below.

TABLE 18

| | Percentage(w/w) of Formulas | | | | | | |
|---|---|---|---|---|---|---|---|
| Ingredients | H | I | J | K | L | M | N |
| Water | 59.8490 | 87.3880 | 32.2390 | 82.2390 | 74.8490 | 75.7490 | 79.5840 |
| Anhydrous Ethyl Alcohol | 20.0000 | 0.01 | 40.9000 | 5.0000 | 15.0000 | 10.0000 | 7.5000 |
| Cyclodextrin and Tea Tree Oil | 5.0000 | 5.0000 | 5.0000 | 5.0000 | 5.0000 | 5.0000 | 5.0000 |
| Polysorbate 20 | 3.0000 | 3.0000 | 3.0000 | 3.0000 | 3.0000 | 3.0000 | 3.0000 |
| Xanthan Gum | 1.0000 | 1.0000 | 1.0000 | 1.0000 | 1.0000 | 1.0000 | 1.0000 |
| Triethanolamine, 99% | 0.6500 | 0.6500 | 0.6500 | 0.6500 | 0.6500 | 0.6500 | 0.6500 |
| Leptospermum Scoparium Oil | 0.2500 | 0.2500 | 0.2500 | 0.2500 | 0.2500 | 0.2500 | 0.2500 |
| Coco Phosphatidyl PG-Dimonium Chloride | 0.5000 | 0.5000 | 0.5000 | 0.5000 | 0.5000 | 0.5000 | 0.5000 |
| Salicylic Acid | 0.5000 | 0.5000 | 0.5000 | 0.5000 | 0.5000 | 0.5000 | 0.5000 |
| Zinc Gluconate | 5.0000 | 0.0001 | 10.0000 | 0.0100 | 2.0000 | 1.5000 | 0.2500 |
| Galactoarabinan | 0.5000 | 0.5000 | 0.5000 | 0.5000 | 0.5000 | 0.5000 | 0.5000 |
| Tocopheryl Acetate | 0.2500 | 0.2500 | 0.2500 | 0.2500 | 0.2500 | 0.2500 | 0.2500 |
| Dipotassium Glycyrrhizinate | 0.2000 | 0.2000 | 0.2000 | 0.2000 | 0.2000 | 0.2000 | 0.2000 |
| DL Panthenol-50% in Water | 0.2000 | 0.2000 | 0.2000 | 0.2000 | 0.2000 | 0.2000 | 0.2000 |
| Cetearyl Octanoate | 0.1000 | 0.1000 | 0.1000 | 0.1000 | 0.1000 | 0.1000 | 0.1000 |
| Titanium Dioxide | 0.1000 | 0.1000 | 0.1000 | 0.1000 | 0.1000 | 0.1000 | 0.1000 |
| Disodium EDTA | 0.1000 | 0.1000 | 0.1000 | 0.1000 | 0.1000 | 0.1000 | 0.1000 |
| Butylene Glycol, Water, and Watercress Extract | 0.1000 | 0.1000 | 0.1000 | 0.1000 | 0.1000 | 0.1000 | 0.1000 |
| Pyridoxine Hydrochloride | 2.5000 | 0.0001 | 5.0000 | 0.1000 | 0.5000 | 0.1000 | 0.0150 |
| Retinyl Palmitate and Tocopherol | 0.0010 | 0.0010 | 0.0010 | 0.0010 | 0.0010 | 0.0010 | 0.0010 |

TABLE 18-continued

| Ingredients | Percentage(w/w) of Formulas | | | | | | |
|---|---|---|---|---|---|---|---|
| | H | I | J | K | L | M | N |
| Butylene Glycol, Water, and Burdock Extract | 0.1000 | 0.1000 | 0.1000 | 0.1000 | 0.1000 | 0.1000 | 0.1000 |
| Aloe Barbadensis Leaf Juice | 0.1000 | 0.1000 | 0.1000 | 0.1000 | 0.1000 | 0.1000 | 0.1000 |
| Total | 100.0000 | 100.0000 | 100.0000 | 100.0000 | 100.0000 | 100.0000 | 100.0000 |

[a]Percentage by weight.

Having illustrated and described the principles of formulations and methods for the topical treatment of oily skin, the art of the invention can be modified in arrangement and detail without departing from such principles. In view of the many possible embodiments to which the principles of my invention can be applied, it should be recognized that the illustrated embodiments are only examples of the invention and should not be taken as a limitation on the scope of the invention. Rather, the scope of the invention is in accord with the following claims. We therefore claim as my invention all that comes within the scope and spirit of these claims.

We claim:

1. A topical composition for reducing sebum on the surface of the skin, comprising an alcohol, pyridoxine or a salt or derivative thereof, and a zinc salt, in an amount sufficient to reduce the amount of sebum on the surface of the skin, wherein the composition comprises:

| Ingredient | Percentage (by weight)[a] |
|---|---|
| Water | about 76% |
| Anhydrous Ethyl Alcohol | about 10% |
| Cyclodextrin and Tea Tree Oil | about 5% |
| Polysorbate 20 | about 3% |
| Xanthan Gum | about 1% |
| Triethanolamine, 99% | about 0.65% |
| Leptospermum Scoparium Oil | about 0.25% |
| Coco Phosphatidyl PG-Dimonium Chloride | about 0.5% |
| Salicylic Acid | about 0.5% |
| Zinc Gluconate | about 0.5% |
| Galactoarabinan | about 0.5% |
| Tocopheryl Acetate | about 0.25% |
| Dipotassium Glycyrrhizinate | about 0.2% |
| DL Panthenol—50% in Water | about 0.2% |
| Cetearyl Octanoate | about 0.1% |
| Titanium Dioxide | about 0.1% |
| Disodium EDTA | about 0.1% |
| Butylene Glycol, Water, and Watercress Extract | about 0.1% |
| Pyridoxine Hydrochloride | about 0.05% |
| Retinyl Palmitate and Tocopherol | about 0.001% |
| Butylene Glycol, Water, and Burdock Extract | about 0.1% |
| Aloe Barbadensis Leaf Juice | about 0.1% |

* * * * *

UNITED STATES PATENT AND TRADEMARK OFFICE
CERTIFICATE OF CORRECTION

PATENT NO. : 6,403,110 B1
DATED : June 11, 2002
INVENTOR(S) : Siddiqui et al.

It is certified that error appears in the above-identified patent and that said Letters Patent is hereby corrected as shown below:

Column 11,
Line 39, Table 5, move "Leaf Juice" up one line to distinguish it from the "Total" line.

Column 14,
Line 15, "Treated" should read -- treated --.

Column 16,
Line 56, "statically" should read -- statistically --.

Column 21,
Line 43, Table 14, "Before Cleansing" should read -- After Cleansing --.

Column 25,
Line 54, Table 17, ""c"" should read -- $^e$ --.

Column 26,
Line 20, "106%" should read -- 100% --.

Column 29,
Line 11, Table 18, move "Leaf Juice" up one line to distinguish it from the "Total" line.

Signed and Sealed this

First Day of July, 2003

JAMES E. ROGAN
*Director of the United States Patent and Trademark Office*